United States Patent
Chow et al.

(10) Patent No.: US 6,534,542 B2
(45) Date of Patent: Mar. 18, 2003

(54) (2-HYDROXY)ETHYL-THIOUREAS USEFUL AS MODULATORS OF $\alpha_{2B}$ ADRENERGIC RECEPTORS

(75) Inventors: Ken Chow, Newport Coast, CA (US); Daniel W. Gil, Corona Del Mar, CA (US); Wenkui Ken Fang, Irvine, CA (US); Michael E. Garst, Newport Beach, CA (US)

(73) Assignee: Allergen Sales, Inc., Irvine, CA (US)

( * ) Notice: Subject to any disclaimer, the term of this patent is extended or adjusted under 35 U.S.C. 154(b) by 11 days.

(21) Appl. No.: 09/794,874

(22) Filed: Feb. 27, 2001

(65) Prior Publication Data

US 2002/0161051 A1 Oct. 31, 2002

(51) Int. Cl.[7] ..................... A61K 31/22; A61K 31/225; A61K 31/17
(52) U.S. Cl. ................. 514/546; 514/548; 514/580; 560/193; 560/251; 564/17
(58) Field of Search ................. 514/546, 548, 514/580; 560/193, 251; 564/17

(56) References Cited

U.S. PATENT DOCUMENTS

| | | | | |
|---|---|---|---|---|
| 2,161,772 A | * | 6/1939 | Carswell ................. | 23/250 |
| 3,686,303 A | * | 8/1972 | Knowles ................. | 260/553 R |
| 6,313,172 B1 | * | 11/2001 | Chow et al. ................. | 514/587 |

FOREIGN PATENT DOCUMENTS

| | | |
|---|---|---|
| GB | 1499485 | 2/1978 |
| WO | 92/0073 | 1/1992 |
| WO | WO-01-00586 A1 | 1/2001 |

OTHER PUBLICATIONS

L'abbe et al., Tetrahedron (1992), 48, pp. 7505–7518.
Messier et al., Pharmacol. Toxicol.(1995), 76, pp. 308–311.
Conklin et al., Nature (1993), 363, pp. 274–276.
Dirig, D.M. et al., J. Neurosci. Methods (1997), 76, pp. 183–191.
Hargreaves, K. et al., Pain (1988), 32, pp. 77–88.
Dixon, W.J., Ann. Rev. Pharmacol. Toxicol. (1980), 20, pp. 441–462.
Reiter, J. et al., Eur. J. Med. Chem.—Chimica Therapeutica, (Jan.–Feb. 1980), 15, pp. 41–53.

* cited by examiner

Primary Examiner—Peter O'Sullivan
(74) Attorney, Agent, or Firm—Gabor L. Szekeres; Carlos A. Fisher; Martin A. Voet

(57) ABSTRACT

Compounds of formula (i) and of formula (ii)

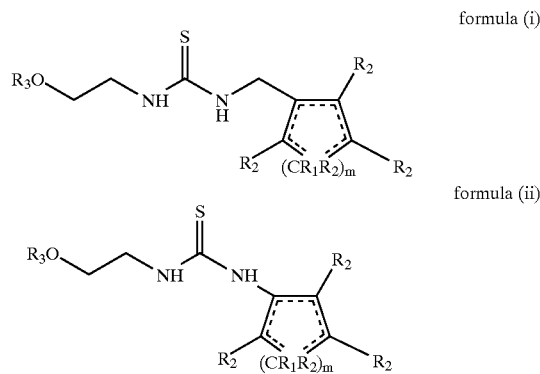

wherein the symbols have the meaning disclosed in the specification, specifically or selectively modulate $\alpha_{2B}$ and/or $\alpha_{2C}$ adrenergic receptors in preference over $\alpha_{2A}$ adrenergic receptors, and as such are useful for alleviating chronic pain and allodynia and have no or only minimal cardiovascular and/or sedatory activity.

54 Claims, No Drawings

(2-HYDROXY)ETHYL-THIOUREAS USEFUL AS MODULATORS OF $\alpha_{2B}$ ADRENERGIC RECEPTORS

BACKGROUND OF THE INVENTION

1. Field of the Invention

The present invention relates to cycloalkyl, cycloalkenyl, cycloalkylmethyl and cycloalkenylmethyl (2-hydroxy) ethylthioureas and their use as specific or selective agonists of $\alpha_{2B}$ adrenergic receptors. More specifically the present invention relates to the above-noted compounds, pharmaceutical compositions containing these compounds as active ingredient for modulating the $\alpha_{2B}$ adrenergic receptors, and even more specifically for utilizing these compounds and pharmaceutical compositions to alleviate chronic pain and allodynia.

2. Background Art

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction). For a further general background on the $\alpha$-adrenergic receptors, the reader's attention is directed to Robert R. Ruffolo, Jr., $\alpha$-Adrenoreceptors: Molecular Biology, Biochemistry and Pharmacology., (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting $\alpha$-adrenergic receptor affinity is explored.

The cloning, sequencing and expression of alpha receptor subtypes from animal tissues has led to the subclassification of the $\alpha_1$ adrenoreceptors into ($\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha 2 adrenergic receptor agonist activity are known analgesics. However, many compounds having such activity do not provide the activity and specificity desirable when treating disorders modulated by alpha-2 adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

British Patent 1 499 485, published Feb. 1, 1978 describes certain thiocarbamide derivatives; some of these are said to be useful in the treatment of conditions such as hypertension, depression or pain.

Certain presently pending applications for patent owned by the the assignee as the present application describe phenylmethyl-(2hydroxy)ethylthioureas which have no significant cardiovascular or sedative effects and are useful for alleviating chronic pain and allodynia.

SUMMARY OF THE INVENTION

The present invention is directed to compounds having formula (i) and formula (ii)

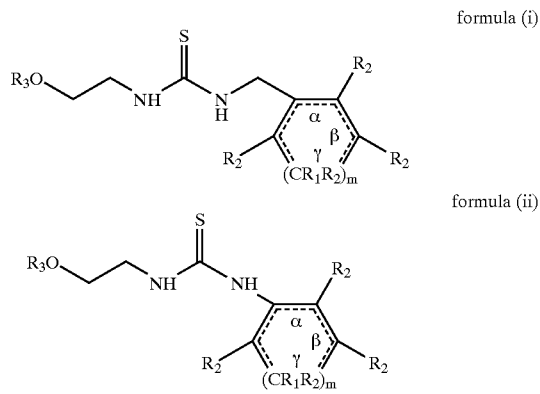

wherein the dotted line represents a bond, or absence of a bond with the provisos that only one dotted line represents a bond in the ring of formula (i) or of formula (ii);

$R_1$ is H, or is absent when the carbon bearing the $R_1$ is double bonded;

$R_2$ is H, alkyl of 1 to 4 carbons, alkenyl of 2 to 4 carbons, alkynyl of 2 to 4 carbons; OH, O-alkyl where the alkyl group has 1 to 4 carbons, $OCOR_4$ where $R_4$ is alkyl of 1 to 4 carbons, F, Cl, Br or I;

m is an integer having the values of 1,2 or 3 with the proviso that when the compound is in accordance with formula (i) and m is 2 then the dotted line designated γ represents absence of a bond, and $R_3$ is H, or $R_4CO$, with the further provisos that when the compound is in accordance with formula (ii) then $R_2$ is not OH, and when the compound is in accordance with formula (ii) and m is 1 then at least one $R_2$ of the five-membered ring is not H.

In a second aspect the present invention is directed to pharmaceutical compositions containing as the active ingredient one or more compounds of formula (i) or of formula (ii), the compositions being utilized as medicaments in mammals, including humans, for treatment of diseases and or alleviations of conditions which are responsive to treatment by agonists of $α_{2B}$ adrenergic receptors. The compositions containing the compounds of the invention are primarily, but not exclusively, used for alleviation of chronic pain and/or allodynia. The compounds have the advantageous property that they are specific or selective to $α_{2B}$ and/or $α_{2C}$ adrenergic receptors in preference over $α_{2A}$ adrenergic receptors, and as such have no or only minimal cardiovascular and/or sedatory activity.

DETAILED DESCRIPTION OF THE INVENTION

A general description of the compounds of the invention is provided in the Summary section of the present application for patent with reference to formula (i) and formula (ii).

enantiomeric as well as in diastereomeric forms. Unless it is specifically noted otherwise, the scope of the present invention includes all trans (E) and cis (Z) isomers, enantiomers and diastereomers. Some of the compounds of the invention may form salts with pharmnaceutically acceptable acid or base, and such pharmaceutically acceptable salts of the compounds of formula (i) and formula (ii) are also within the scope of the invention.

Referring now to formulas (i) an (ii), in most of the preferred compounds of the invention the symbol m represents an integer having the values 1 or 2; in other words the ring depicted in formula (i) and formula (ii) is either 5 or 6 membered. The $R_2$ group is preferably hydrogen, alkyl, chloro or bromo and the $R_3$ group is preferably hydrogen, acetyl ($CH_3CO$—) or other group subject to hydrolyis under physiological conditions.

The presently most preferred compounds of the invention are disclosed in Table 1 with reference to Formula 1, and in Table 2 with reference to Formula 2. It should be readily apparent from this disclosure that the preferred compounds of Formula 1 are in the scope of the formula (i), and that the preferred compounds of Formula 2 are in the scope of formula (ii).

Formula 1

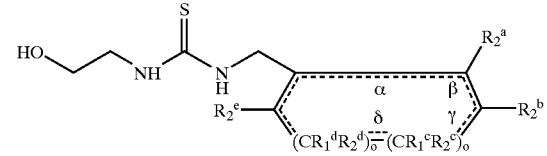

TABLE 1

| Compound No. | dotted line that represents a double bond | $R_2^a$ | $R_2^b$ | $R_2^c$ | $R_1^c$ | $R_2^d$ | $R_1^d$ | o | p | $R_2^e$ | $R_3$ |
|---|---|---|---|---|---|---|---|---|---|---|---|
| 19 | β | H | ethyl | H | H | H | H | 1 | 1 | H | H |
| 20 | β | H | methyl | H | H | H | H | 1 | 1 | H | H |
| 1 | — | H | H | H | H | H | H | 1 | 1 | H | H |
| 8 | δ | H | H | H | — | H | — | 1 | 1 | H | H |
| 10 | — | H | H | H | H | H | H | 2 | 1 | H | H |
| 3 | α | H | H | H | H | H | H | 1 | 1 | H | H |
| 4 | β | H | H | H | H | H | H | 1 | 1 | H | H |
| 9 | — | H | H | H | H | — | — | 1 | 0 | H | H |
| 42 | — | H | H | H | H | H | H | 1 | 1 | H | $CH_3CO$ |
| 26 | β | n-butyl | H | H | H | — | — | 1 | 0 | H | H |
| 25 | α | n-butyl | H | H | H | — | — | 1 | 0 | H | H |
| 27 | α | methyl | H | H | H | — | — | 1 | 0 | H | H |
| 28 | α | H | methyl | H | H | — | — | 1 | 0 | H | H |
| 21 | β | methyl | H | H | H | H | H | 1 | 1 | H | H |
| 22 | β | ethyl | H | H | H | H | H | 1 | 1 | H | H |
| 11 | δ | methyl | H | H | — | H | — | 1 | 1 | H | H |
| 23 | α | methyl | H | H | H | H | H | 1 | 1 | H | H |
| 24 | α | ethyl | H | H | H | H | H | 1 | 1 | H | H |
| 17 | α | Cl | H | H | H | H | H | 1 | 1 | H | H |
| 18 | α | Br | H | H | H | H | H | 1 | 1 | H | H |

It will be readily apparent to those skilled in the art that some of the compounds depicted in these formulas may exist in trans (E) and cis (Z) isomeric forms. Moreover, some of the compounds of the invention may contain one or more asymmetric centers, such that the compounds may exist in

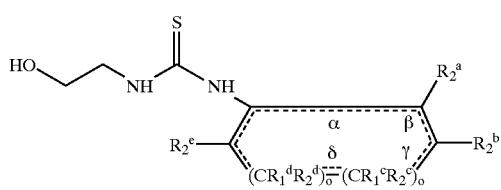

Formula 2

TABLE 2

| Compound No. | dotted line that represents a double bond | $R_2^a$ | $R_2^b$ | $R_2^c$ | $R_1^c$ | $R_2^d$ | $R_1^d$ | o | p | $R_2^e$ |
|---|---|---|---|---|---|---|---|---|---|---|
| 40 | — | H | H | $CH_3$ | H | H | H | 1 | 1 | H |
| 5 | — | n-propyl | H | H | H | H | H | 1 | 1 | H |
| 41 | — | methyl* | H | H | H | H | H | 1 | 1 | H |
| 13 | β | H | $CH_3$ | H | H | — | — | 1 | 0 | H |
| 14 | β | methyl | H | H | H | — | — | 1 | 0 | H |
| 12 | — | methyl | H | H | H | — | — | 1 | 0 | H |
| 16 | β | H | methyl | H | H | H | H | 1 | 1 | H |
| 33 | β | methyl | H | H | H | H | H | 1 | 1 | H |
| 34 | β | ethyl | H | H | H | H | H | 1 | 1 | H |
| 35 | β | H | H | H | H | H | H | 1 | 1 | H |
| 31 | β | methyl | methyl | H | H | H | H | 1 | 1 | H |
| 30 | β | n-propyl | H | H | H | H | H | 1 | 1 | H |
| 29 | β | Br | H | H | H | H | H | 1 | 1 | H |
| 38 | — | H | methyl* | H | H | H | H | 1 | 1 | H |
| 39 | — | H | methyl** | H | H | H | H | 1 | 1 | H |
| 36 | — | H | H | ethyl* | H | H | H | 1 | 1 | H |
| 2 | — | Isopropyl* | H | H | H | methyl** | H | 1 | 1 | H |
| 6 | — | H | H | H | H | H | H | 1 | 1 | H |
| 7 | — | H | H | OH | H | H | H | 1 | 1 | H |
| 15 | β | methyl | methyl | H | H | — | — | 1 | 0 | H |
| 32 | β | H | ethyl | H | H | H | H | 1 | 1 | H |
| 37 | — | ethyl* | H | H | H | H | H | 1 | 1 | H |

*trans relative to the NH group.
**cis relative to the NH group.

Generally speaking, the compounds of the invention can be obtained in accordance with reaction of an isothiocyanate intermediate which is in accordance with Formula 3 or in accordance with Formula 4, and an amine intermediate, which is in accordance with Formula 5 (ethanolamine, or protected ethanolamine, $R_3$ in Formula 5 is H or an acyl group such as $CH_3CO$, or a removable protective group). The reaction of an isothiocyanate intermediate in accordance with Formula 3 or in accordance with Formula 4 with an amine in accordance with Formula 5 is described in detail in the experimental section of this application and is generally referred to as General Procedure A.

Alternatively compounds of the invention can be obtained by reaction of a protected isothiocyanate such as of Formula 6 (t-butyldimethylsilyloxyethyl isothiocyanate) or of Formula 7 (acetic acid 2-isothiocyanato-ethyl ester) with an amine of Formula 8 or of Formula 9, followed by appropriate reactions removing any protecting groups. The reaction of t-butyldimethylsilyloxyethyl isothiocyanate (Formula 6) with an amine of Formula 8 or of Formula 9 is described in detail in the experimental section of this application and is generally referred to as General Procedure B.

The reaction between an isothiocyanate and an amine, to provide a thiourea derivative per se is well known in the art. Typically such reactions are performed in an aprotic solvent, such as toluene, in the presence of a catalytic amount of base, such as dimethylaminopyridine (DMAP). These reactions are illustrated in Reaction Scheme 1, (where the symbols have their previously defined meaning) although it should be understood that variations in the protecting groups used, as well as in the reaction conditions are possible and within the skill of the practicing organic chemist in light of the present disclosure.

REACTION SCHEME 1

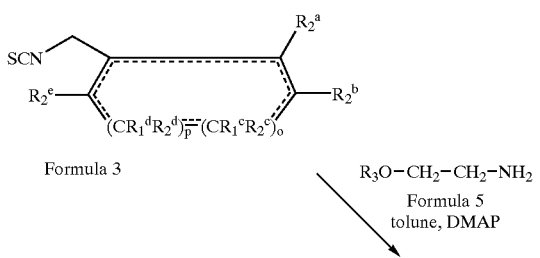

Formula 3

$R_3O-CH_2-CH_2-NH_2$

Formula 5
tolune, DMAP

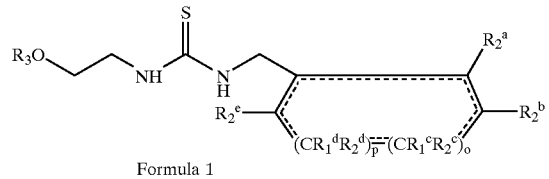

Formula 1

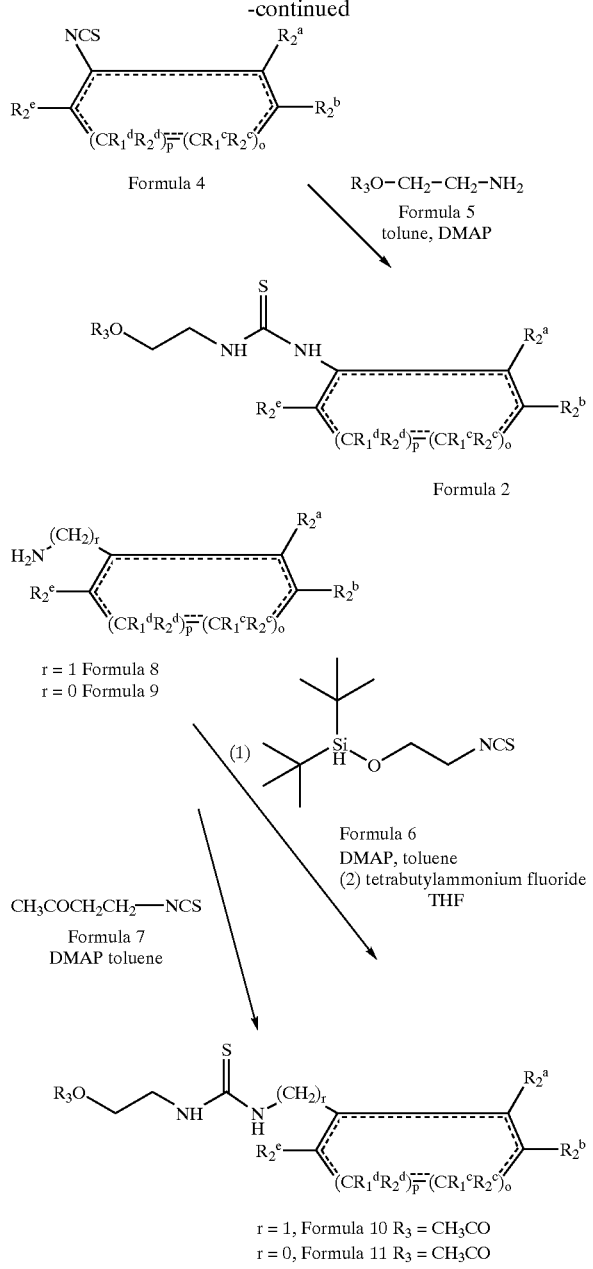

The reagent t-butyldimethylsilyloxyethyl isothiocyanate (Formula 6) can be obtained as described by L'abbe et al. Tetrahedron 1992, 48, 7505–7518.

The reagent acetic acid 2-isothiocyanato-ethyl ester (Formula 7) can be obtained as described in the experimental below.

The cycloalkyl or cycloalkenyl isothiocyanates of Formulas 3 and 4 and the cycloalkyl or cycloalkenyl amines of Formulas 8 and 9 can, generally speaking, be obtained in accordance with the chemical literature, and/or by such modifications of known synthetic procedures which will be readily apparent to those skilled in the art in light of the present disclosure. The reaction schemes incorporated in the experimental section of this application generally illustrate the synthetic schemes which are employed for the synthesis of preferred embodiments of compounds of the invention.

Biological Activity, Modes of Administration

The compounds of the invention are agonists of $\alpha_2$ adrenergic receptors, particularly they tend to be specific or selective agonists of $\alpha_{2B}$ and/or to a lesser extent $\alpha_{2C}$ adrenergic receptors, in preference over $\alpha_{2A}$ adrenergic receptors. The specific or selective $\alpha_{2B}$ and/or to a lesser extent $\alpha_{2C}$ agonist activity of the compounds of the invention is demonstrated in an assay titled Receptor Selection and Amplification technology (RSAT) assay, which is described in the publication by Messier et. Al., 1995, Pharmacol. Toxicol. 76, pp. 308–311 (incorporated herein by reference) and is also described below. Another reference pertinent to this assay is Conklin et al. (1993) Nature 363:274–6, also incorporated herein by reference.

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, $G_q$, elicit this response. Alpha$_2$ receptors, which normally couple to $G_i$, activate the RSAT response when coexpressed with a hybrid $G_q$ protein that has a $G_i$ receptor recognition domain, called $G_{q/i5}^2$.

NIH-3T3 cells are plated at a density of $2\times10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5–10 μg), receptor (1–2 μg) and G protein (1–2 μg). 40 μg salmon sperm DNA may also be included in the transfection mixture. Fresh media is added on the following day and 1–2 days later, cells are harvested and frozen in 50 assay aliquots. Cells are thawed and 100 μl added to 100 μl aliquots of various concentrations of drugs in triplicate in 96-well dishes. Incubations continue 72–96 hr at 37°. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30 and measuring optical density at 420 nm. The absorbance is a measure of enzyme activity, which depends on cell number and reflects a receptor-mediated cell proliferation. The $EC_{50}$ and maximal effect of each drug at each alpha$_2$ receptor is determined. The efficacy or intrinsic activity is calculated as a ratio of the maximal effect of the drug to the maximal effect of a standard full agonist for each receptor subtype. Brimonidine, also called UK514304, the chemical structure of which is shown below, is used as the standard agonist for the alpha$_{2A}$, alpha$_{2B}$ and alpha$_{2C}$ receptors.

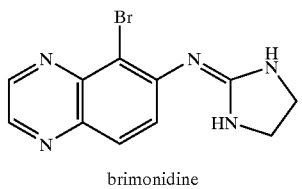
brimonidine

The results of the RSAT assay with several exemplary compounds of the invention are disclosed in Table 3. Each number in the table represents $EC_{50}$ in nanomolar (nM) concentration whereas the number in parenthesis in the table shows the fraction of activity of the appropriate standard which is attained by the tested compound. NA stands for "not active" at concentrations less than 10 micromolar. As is known $EC_{50}$ is the concentration at which half of a given compound's maximal activity is observed. It can be seen from the table that the compounds of the invention are specific or selective agonists of $\alpha_{2B}$ and/or $\alpha_{2C}$ adrenergic receptors, with no agonist like activity or only with insignificant agonist-like activity on $\alpha_{2A}$ receptors.

The discovery of compounds, such as the present ones, which have specific of selective activity on $\alpha_{2B}$ adrenergic receptors with no activity or only minimal acticity on $\alpha_{2A}$ is in and of itself another significant aspect of the invention, inasmuch as to the best knowledge of the present inventors the ability to bifurcate the activity on these two receptors has not been known in the prior art.

Thus, the compounds of the invention are useful for treating conditions and diseases which are responsive to treatment by $\alpha_{2B}$ adrenergic receptor agonists. Such conditions and diseases include, but are not limited to, chronic pain, visceral pain, neuropathic pain, corneal pain, glaucoma, ischemic neuropathies and other neurodegenerative diseases. The lack of substantial activity or total lack of activity of the compounds of the invention at $\alpha_{2A}$ receptors is highly advantageous because the administration of these compounds to mammals does not result in sedation or in significant cardiovascular effects (such as changes in blood pressure or heart rate).

TABLE 3

| Compound No. | RSAT $EC_{50}$ (nM) | | |
|---|---|---|---|
| | Alpha 2A | Alpha 2B | Alpha 2C |
| 19 | NA | 55 (0.46) | NA |
| 20 | NA | 37 (0.78) | NA |
| 1 | NA | 204 (0.61) | NA |
| 8 | NA | 17 (0.79) | NA |
| 10 | NA | 355 (0.54) | NA |
| 40 | NA | 57 (0.62) | NA |
| 5 | NA | 216 (0.49) | NA |
| 41 | NA | 27 (0.78) | NA |
| 3 | NA | 877 (0.8) | NA |

TABLE 3-continued

| Compound No. | RSAT $EC_{50}$ (nM) | | |
|---|---|---|---|
| | Alpha 2A | Alpha 2B | Alpha 2C |
| 4 | NA | 66 (0.63) | NA |
| 9 | NA | 441 (0.62) | NA |
| 26 | NA | 816 (0.48) | NA |
| 25 | NA | >2000 (0.51) | 738 (0.69) |
| 27 | NA | 135 (0.75) | 1729 (0.3) |
| 28 | NA | 544 (0.52) | NA |
| 13 | NA | 111 (0.66) | NA |
| 14 | NA | 97 (0.95) | 3000 (0.3) |
| 15 | 515 (0.4) | 5 (1.08) | 197 (0.4) |
| 12 | NA | 1532 (0.47) | NA |
| 21 | NA | 72 (0.87) | NA |
| 22 | NA | 126 (0.73) | NA |
| 11 | NA | 20 (0.93) | |
| 23 | NA | 125 (0.68) | NA |
| 24 | NA | 772 (0.71) | NA |
| 16 | NA | 58 (0.54) | NA |
| 33 | NA | 12 (0.71) | 251 (0.98) |
| 32 | NA | 96 (0.37) | NA |
| 34 | NA | 11 (0.88) | 59 (0.62) |
| 35 | NA | 73 (0.58) | 630 (0.4) |
| 31 | NA | 6 (0.8) | 253 (0.37) |
| 30 | NA | 78 (0.71) | |
| 29 | NA | 90 (0.84) | |
| 17 | NA | 15 (0.63) | |
| 18 | NA | 10 (0.77) | |
| 37 | 14 (0.4) | 2 (0.93) | 106 (0.4) |
| 38 | NA | 1151 (0.4) | Na |
| 39 | NA | 80 (0.65) | NA |
| 36 | NA | 97 (0.53) | NA |
| 2 | NA | 189 (0.54) | |
| 6 | NA | 311 (0.28) | NA |
| 7 | NA | >2000 (0.32) | |

The compounds of the invention act and can be used as a highly effective analgesic, particularly in chronic pain models, with minimal undesirable side effects, such as sedation and cardiovascular depression, commonly seen with other agonists of the $\alpha_2$ receptors.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1–1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula (i) and of Formula (ii) and armaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more compounds of Formula (i) or of Formula (ii) or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A$\beta$ and A$\delta$ fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A$\beta$ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

The following in vivo assays can be employed to demonstrate the biological activity of the compounds of the invention.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (ie. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

Compound 40 of the invention was tested in this assay intraperitoneally and up to a dose of 300 $\mu$g/kg, and was found to have no sedative effect.

The results in this test with other compounds of the invention are also expected to show that the compounds of the invention are not sedating.

Effects on Cardiovascular System

To test the effect of the compounds on the cardiovascular system, typically six cynomolgus monkeys are given 500 $\mu$g/kg of the test compound by intravenous injection (i.v.). The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results in this test are expected to show that the compounds of the invention have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183–191 (1997) and Hargreaves, K. et al., *Pain* 32:77–88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Typically four test animals per group are weighed (approximately 0.3 kg) and injected intraperitonealy (i.p.) with 1 ml/kg of the test compound formulated in approximately 10 to 50% dimethylsulfoxide (DMSO) vehicle. Animals typically receive a 0.3 mg/kg and a 3 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45–50 degrees centigrade to each rat hindpaw.

The results in this test are expected to show that the compounds of the invention do not provide analgesic effects in this bioassay of acute pain.

Alleviation of Chronic Pain

A model for chronic pain (in particular peripheral neuropathy such as causalgia) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transyerse process is carefully removed with a small rongeur to expose the L4–L6 spinal nerves. The L5 and L6 spinal nerves are isolated and tightly ligated with 6-0 silk thread. The same procedure is done on the right side as a control, except no ligation of the spinal nerves is performed. A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in approximately 10 to 50% DMSO and given in a volume of 1 ml/kg body weight.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6–8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1–2 gram hair. The 50% paw withdrawal threshold is determined using the method of Dixon, W. J., *Ann. Rev. Pharmacol. Toxicol.* 20:441–462 (1980). The post-drug threshold is compared to the pre-drug threshold and the percent reversal of tactile sensitivity is calculated based on a normal threshold of 15.1 grams. The results are expressed in per cent (%) MPE, where the MPE value reflects the percentage reversal of pain threshold to that of a normal animal (100%). Table 4 below indicates results of this test with Compounds 8, 34 and 40 of the invention, administered i.p., in intrathecal and oral doses. The doses and the observed MPE values (±SEM) are shown in the table.

TABLE 4

| IP Doses | % MPE | | |
|---|---|---|---|
| | Compound 34 | Compound 8 | Compound 40 |
| 10 μg/kg | 0.4 ± 1.0 | 1.5 ± 0.9 | 0.1 ± 1.8 |
| 30 μg/kg | 48 ± 6.1 | 47 ± 8.6 | 42 ± 9.2 |
| 100 μg/kg | 66 ± 11 | 63 ± 9.1 | 46 ± 7.1 |
| 300 μg/kg | 96 ± 3.7 | 56 ± 6.5 | 77 ± 8.0 |
| 1000 μg/kg | | 52 ± 8.4 | 83 ± 7.0 |
| 3000 μg/kg | | | 90 ± 6.1 |
| Intrathecal Doses | | | |
| 30 μg | | 0.02 ± 0.6 | |
| 100 μg | | 1.3 ± 0.6 | |
| 300 μg | | 20 ± 5.1 | |
| Oral Dose | | | |
| 1000 μg/kg | | | 80 ± 6.1 |

The results showed in Table 4 illustrate that these compounds of the invention significantly alleviate allodynic pain, and based on these test and of the compounds ability to activate $\alpha_{2B}$ adrenergic receptors in preference over $\alpha_{2A}$ adrenergic receptors, the compounds of the invention are expected to be useful as analgesics to alleviate allodynia and chronic pain.

General Procedure A for the Synthesis of Hydroxyethyl Cycloalkanylmethyl or Cycloalkenylmethyl and Cycloalkanyl Thioureas:

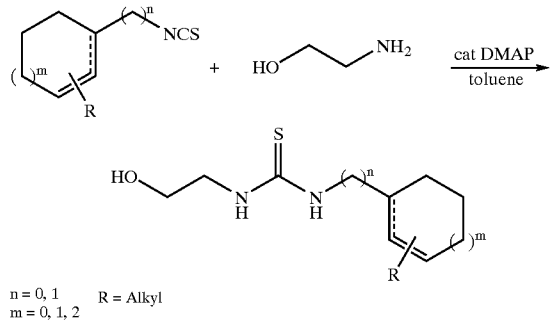

The isothiocyanate (prepared from the corresponding azide according to the procedure described by L'abbe et al. Tetrahedron 1992, 48, 7505–7518, and ethanolamine (2–3 eq) were mixed in toluene, followed by the addition of catalytic amount of 4-(N,N-dimethylamino)pyridine (DMAP). The resulting reaction mixture was stirred at room temperature for 14 hours, then concentrated. Chromatography (gradient solvent system, from 50% EtOAc/Hexanes to 10% MeOH/EtOAc) gave the desired product.

General Procedure B for the Synthesis of Hydroxyethyl Cycloalkanylmethyl or Cycloalkenylmethyl and Cycloalkanyl Thioureas:

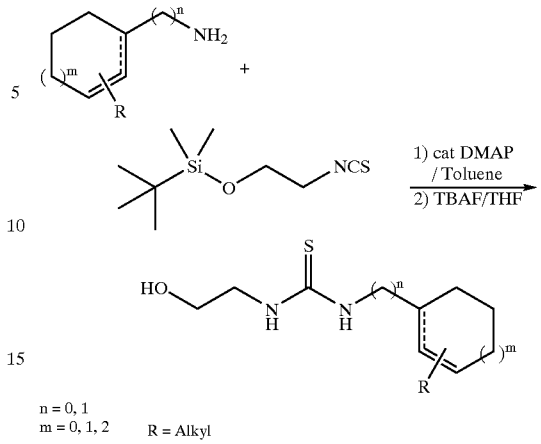

Butyldimethylsilyloxyethyl isothiocyanate (prepared from t-butyldimethylsilyloxyethyl bromide according to the procedure described L'abbe et al. (see above) and substituted cycloalkylmethylamine or cycloalkenylmethylamine or cycloalkylamine (2–3 eq) were mixed in toluene, followed by the addition of catalytic amount of DMAP. The resulting reaction mixture was stirred at room temperature for 14 hours, then concentrated. Deprotection with tetra-n-butylammonium fluoride (TBAF) in tetrahydrofuran (THF) gave the crude product, which was chromatographed (gradient solvent system, from 50% EtOAc/Hexanes to 10% MeOH/EtOAc) to afford the desired product.

Proton nuclear magnetic resonance ($^1$H NMR) spectra were recorded on a Varian 300 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; br, broad; m, multiplet. Data were reported in the following format: chemical shift (multiplicity, coupling constant(s) J in Hertz (Hz) integrated intensity).

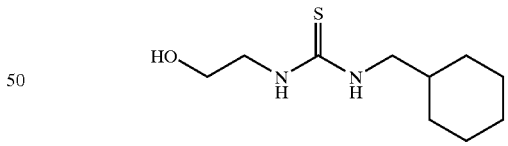

1-Cyclohexylmethyl-3-(2-hydroxy-ethyl)-thiourea
(Compound 1)

The title compound was obtained (3.50 g, 81%) from commercially available cyclohexylmethyl isothiocyanate (3.10 g) and ethanolamine (4.00 mL) according to General Procedure A. Spectroscopic data: $^1$H NMR (D$_6$ DMSO, 300 MHz) δ 7.48 (br s, 1H), 7.29 (br s, 1H), 4.73 (br s, 1H), 3.50–3.35 (m, 4H), 3.20 (br s, 2H), 1.70–1.54 (m, 6H), 1.45 (br s, 1H), 1.25–1.06 (m, 4H), 0.95–0.80 (m, 2H).

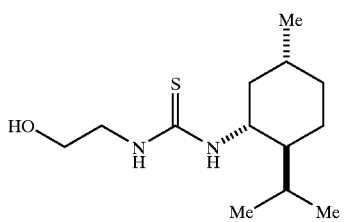

1-(2-Hydroxy-ethyl)-3-(1R,2S,5R-2-isopropyl-5-methyl-cyclohexyl)-thiourea (Compound 2)

The title compound was obtained (1.33 g, 89%) from commercially available 1R,2S,5R-2-isopropyl-5-methyl-cyclohexylamine and t-butyldimethylsilyloxyethyl isothiocyanate (2.00 g) according to General Procedure B. Spectroscopic data: $^1$H NMR (D$_6$ DMSO, 300 MHz) δ 7.26 (d, J=9.08 Hz, 1H), 7.14 (br s, 1H), 4.76 (br s, 1H), 4.01 (br s, 1H), 3.45 (m, 4H), 1.98–1.76 (m, 2H), 1.71–1.52 (m, 2H), 1.45–1.28 (m, 2H), 1.23–0.88 (m, 3H), 0.85 (d, J=6.74 Hz, 6H), 0.73 (d, J=6.74 Hz, 3H).

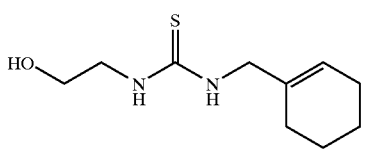

1-(Cyclohex-1-enylmethyl)-3-(2-hydroxy-ethyl)-thiourea (Compound 3)

To a solution of LAH (195 mg, 5.14 mmol, 1 eq) in ether at 0° C. was added 500 mg (4.7 mmol) of commercially available cyclohex-1-enecarbonitrile. After 1 hour, the reaction is quenched with water and filtered through celite. The filtrate was distilled off to give 430 mg (83% yield) of cyclohex-1-enyl-methylamine. Spectroscopic data: $^1$H NMR (CDCl$_3$, 300 MHz) δ=1.52–1.63 (m, 5H), 1.91–2.00 (m, 5H), 3.10 (s, 2H), 5.52 (br s, 1H). The title compound was obtained from cyclohex-1-enyl-methylamine (430 mg, 3.87 mmol) and tert-butyl(2-isothiocyanato-ethoxy)dimethyl-silane (679 mg, 1 eq) according to the General Procedure B. Spectroscopic data: $^1$H NMR (D$_6$ DMSO, 300 MHz) δ=1.48–1.58 (m, 4H), 1.88 (br s, 2H), 1.95 (br s, 2H), 3.46 (br s, 4H), 3.92 (br s, 2H), 4.74 (br s, 1H), 5.5 (br s, 1H), 7.35 (br s, 1H), 7.50 (br s, 1H).

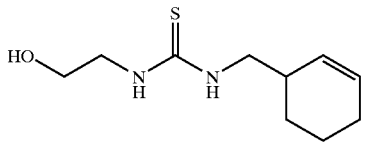

1-(Cyclohex-2-enylmethyl)-3-(2-hydroxy-ethyl)-thiourea (Compound 4)

A solution of commercially available 3-bromo-cyclohexene (2.0 g, 12.42 mmol) and CuCN (1.2 g, 1.1 eq) in dimethylformamide was stirred at room temperature overnight. Distillation gave 1.2 g (60% yield) of the desired cyclohex-2-enecarbonitrile. Spectroscopic data: $^1$H NMR (CDCl$_3$, 300 MHz) δ=1.65–2.11 (m, 6H), 3.21–3.27 (m, 1H), 5.60–5.66 (m, 1H), 5.91–5.97 (m, 1H). The nitrile (360 mg, 3.36 mmol) was then added to a solution of LAH (1 eq) in ether at 0° C. After 1 hour, the reaction was quenched with water and filtered through celite. The filtrate was distilled off to give 175 mg (47% yield) of 2-cyclohexene-yl-methyl amine. Spectroscopic data: $^1$H NMR (D$_6$ DMSO, 300 MHz) δ=1.23–1.33 (m, 4H), 1.50–1.57 (m, 2H), 1.72–1.80 (m, 2H), 1.96–2.00 (m, 2H), 2.14 (br s, 1H), 5.56–5.59 (m, 1H), 5.75–5.78 (m, 1H).

The title compound was obtained from 2-cyclohexene-yl-methyl amine (175 mg, 1.60 mmol) and tert-butyl-(2-isothiocyanato-ethoxy)dimethyl-silane (553 mg, 1 eq) according to General Procedure B. Spectroscopic data: $^1$H NMR (D$_6$ DMSO, 300 MHz) δ=1.18–1.26 (m, 1H), 1.41–1.48 (m, 1H), 1.65–1.70 (m, 2H), 1.94 (br s, 2H), 2.32 (br s, 1H), 3.30 (br s, 1H), 3.43–3.47 (m, 5H), 4.76 (br s, 1H), 5.55 (dd, 1H, J=10 Hz), 5.69–5.73 (m, 1H), 7.38 (br s, 1H), 7.55 (br s, 1H).

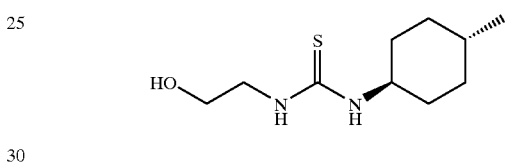

1-(2-Hydroxy-ethyl)-3-(4-methyl-cyclohexyl)-thiourea (Compound 40)

The title compound was obtained from 2.0 g of commercially available 4-methylcyclohexylamine (17.7 mmol) and tert-butyl-(2-isothiocyanato-ethoxy)dimethyl-silane (3.2 g) according to General Procedure B. Spectroscopic data: $^1$H NMR (D$_6$ DMSO, 300 MHz) δ=0.845 (d, J=6.84 Hz, 3H)), 0.89–0.97 (m, 2H), 1.09–1.11 (m, 2H), 1.26–1.30 (m, 1H), 1.63–1.65 (m, 2H), 1.87–1.89 (m, 2H), 3.42–3.46 (m, 4H), 3.86 (br s, 1H), 4.73 (br s, 1H), 7.19 (s, 1H), 7.30 (d, J=8.30 Hz, 1H)).

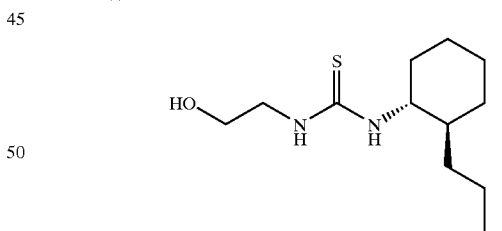

1-(2-Hydroxy-ethyl)-3-((1R,2R)-2-propyl-cyclohexyl)-thiourea (Compound 5)

The title compound was obtained from (−)-trans-2-propylcyclohexylamine (2.0 g, 14.2 mmol) and tert-butyl-(2-isothiocyanato-ethoxy)dimethyl-silane (2.5 g) according to General Procedure B. Spectroscopic data: $^1$H NMR (D$_6$ DMSO, 300 MHz) δ=0.84 (t, J=6.89 Hz, 3H), 0.92–1.48 (m, 8H), 1.61 (br s, 2H), 1.77–1.92 (m, 2H), 3.46 (br s, 5H), 3.86 (br s, 1H), 4.76 (br s, 1H), 7.19 (br s, 1H), 7.305 (d, J=8.50 Hz, 1H).

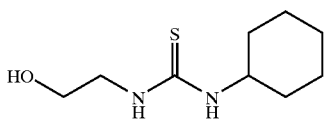

1-Cyclohexyl-3-(2-hydroxy-ethyl)-thiourea (Compound 6)

The title compound was obtained from 4.34 g (43.76 mmol) of cyclohexylamine and tert-butyl-(2-isothiocyanato-ethoxy)dimethyl-silane (8.4 g) according to General Procedure B. Spectroscopic data: $^1$H NMR (D6 DMSO, 300 MHz) δ=1.09–1.16 (m, 3H), 1.21–1.29 (m, 2H), 1.51–1.53 (m, 1H), 1.61–1.65 (m, 2H), 1.80–1.83 (m, 2H), 3.42–3.46 (m, 4H), 3.95 (br s, 1H), 4.73 (br s, 1H), 7.23 (br s, 1H), 7.355 (d, J=8.30 Hz, 1H).

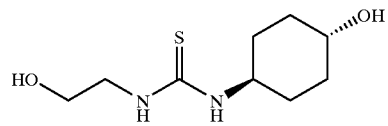

1-(4-Hydroxy-cyclohexyl)-3-(2-hydroxy-ethyl)-thiourea (Compound 7)

The title compound was obtained from 1.0 g of 4-hydroxycyclohexylamine (6.60 mmol) and tert-butyl-(2-isothiocyanato-ethoxy)dimethyl-silane (700 mg) according to General Procedure B in CH$_2$Cl$_2$ in the presence of triethylamine (TEA) and DMAP as catalyst. Spectroscopic data: $^1$H NMR (D$_6$ DMSO, 300 MHz) δ=1.08–1.25 (m, 4H), 1.77–1.88 (m, 4H), 3.36–3.47 (m, 5H), 3.87 (br s, 1H), 4.515 (d, J=4.39 Hz, 1H), 4.75 (br s, 1H), 7.24 (br s, 1H), 7.325 (d, J=7.91 Hz, 1H).

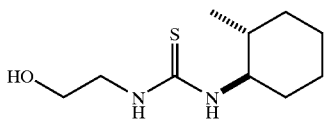

1-(2-Methyl-cyclohexyl)-3-(2-hydroxy-ethyl)-thiourea (Compound 41)

The title compound was obtained from commercially available 2-methylcyclohexylamine (5.0 g, 44.24 mmol) and tert-butyl-(2-isothiocyanato-ethoxy)dimethyl-silane (7.8 g, 1 eq) according to General Procedure B. The relative stereochemistry was confirmed by preparing the thiourea from cis-2-methylcyclohexanol as described in General Procedure D. Spectroscopic data: $^1$H NMR (DMSO) δ=0.84 (d, 3OH, J=10 Hz), 0.96–1.02 (m, 2H), 1.11–1.24 (m, 2H), 1.33 (br s, 1H), 1.57–1.71 (m, 3H), 1.90 (br s, 1H), 3.42–3.47 (m, 4H), 3.77 (br s, 1H), 4.75 (br s, 1H), 7.18 (br s, 1H), 7.31 (d, 1H, J=10 Hz).

General Procedure D for the synthesis of hydroxyethyl thioureas:

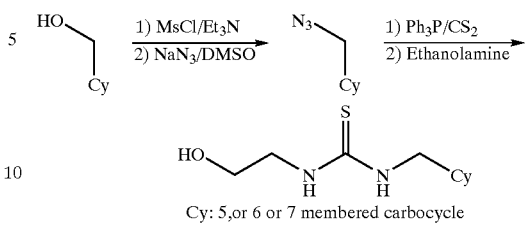

Cy: 5, or 6 or 7 membered carbocycle

The alcohol was dissolved in dichloromethane, then cooled to −78° C. Triethylamine and mesyl chloride were added. The resulting reaction mixture was allowed to warm to room temperature over 2 hours, then diluted with ether. The organic layer was washed with water and brine, then dried over magnesium sulfate and concentrated to afford the crude mesylate, which was dissolved in DMSO, and treated with sodium azide either at room temperature or at 65° C. depending on the substrate for 14 hours. The reaction mixture was cooled (if necessary) to room temperature and diluted with water. After extraction of the mixture with ether, the combined ether layers were washed with water and brine, then dried over magnesium sulfate and concentrated to yield the crude azide. This crude azide was dissolved in carbon disulfide and treated with triphenylphosphine at room temperature for 6 hours, then refluxed for 3 hours. The reaction mixture was concentrated, then diluted with hexane. The solids formed were washed with more hexane, and the combined organic phases were concentrated to give the crude isothiocyanate. The title compound was obtained from this isothiocyanate and ethanolamine according to General Procedure A.

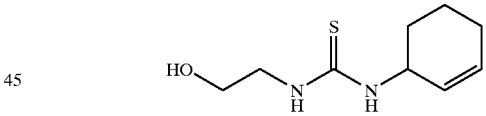

1-Cyclohex-3-enylmethyl-3-(2-hydroxy-ethyl)-thiourea (Compound 8)

Sodium borohydride in methanol was added to a solution of commercially available 3-cyclohexene-1-carboxaldehyde in methanol at 0° C. and the resulting reaction mixture was stirred for 30 minutes, then diluted with ethyl acetate. The organic layer was washed with water and then dried over magnesium sulfate and concentrated to give the crude alcohol. The crude alcohol without further purification was converted to the title compound as described in General Procedure D. Spectroscopic data: $^1$H NMR (D$_6$ DMSO, 300 MHz) δ 7.55 (br s, 1H), 7.34 (br s, 1H), 5.61 (br s, 2H), 4.76 (br s, 1H), 3.45 (br s, 4H), 3.30 (br s, 2H), 2.10–1.92 (m, 3H), 1.83–1.58 (m, 3H), 1.25–1.10 (m, 1H).

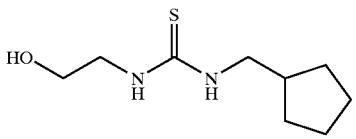

1-Cyclopentylmethyl-3-(2-hydroxy-ethyl)-thiourea (Compound 9)

The intermediate azidomethylcyclopentane was obtained from commercially available cyclopentanemethanol as described in General Procedure D. Spectroscopic data: $^1$H NMR (CDCl$_3$, 300 MHz) δ 3.18 (d, J=10.0 Hz, 2H), 2.23–2.05 (m, 1H), 1.87–1.74 (m, 2H), 1.68–1.55 (m, 4H), 1.30–1.15 (m, 2H). The azide was then converted into cyclopentylmethyl isothiocyanate, which was reacted with ethanolamine to afford the title compound (12.68 g, 63%) according to General Procedure A. Spectroscopic data: $^1$H NMR (D$_6$, DMSO, 300 MHz) δ 7.46 (br s, 1H), 7.31 (br s 1H), 4.72 (br s, 1H), 3.5–3.38 (m, 4H), 3.25 (br s, 2H), 2.03 (quintet, J=6.4 Hz, 1H), 1.70–1.57 (m, 3H), 1.55–1.41 (m, 3H), 1.20–1.10 (m, 2H).

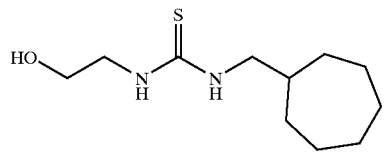

1-Cycloheptylmethyl-3-(2-hydroxy-ethyl)-thiourea (Compound 10)

Commercially available cycloheptanecarboxylic acid (25 g) was dissolved in methanol (150 ml), then sulfuric acid (2 mL) was added. The resulting reaction mixture was refluxed for 4 hours then neutralized with saturated aqueous sodium bicarbonate solution. The mixture was concentrated and then diluted with ether. The ethereal solution was washed with water and brine, then dried over magnesium sulfate and concentrated to give 26 grams (95%) of the desired methyl ester. 10 grams of this ester was dissolved in THF (100 mL), then cooled to –78° C. LAH (64.00 mL, 1.0 M in THF) was added, and the resulting reaction was allowed to warm to room temperature over 60 minutes. The reaction was quenched with water and sodium hydroxide. The solids formed were washed with ether, and the combined organic phases were dried over magnesium sulfate and concentrated to give a quantitative yield (8.00 g) of the desired cycloheptanemethanol. The title compound was obtained (9.52 g, 66% based on the intermediate cycloheptanemethanol) from this cycloheptanemethanol according to General Procedure D. Spectroscopic data: $^1$H NMR (D$_6$ DMSO, 300 MHz) δ 7.46 (br s, 1H), 7.28 (br s, 1H), 4.72 (br s, 1H), 3.51–3.36 (m, 4H), 3.20 (br s, 2H), 1.72–1.28 (m, 11H), 1.18–1.03 (m, 2H).

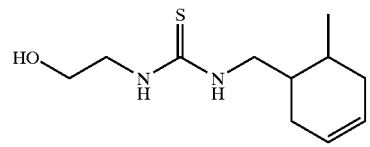

Synthesis of 1-(2-hydroxy-ethyl)-3-(6-methyl-cyclohex-3-enylmethyl)-thiourea (Compound 11)

The title compound was generated from commercially available (6-methyl-cyclohex-3-enyl)-methanol according to General Procedure D. Spectroscopic data: $^1$H NMR (DMSO) δ=0.94 (d, 3H, J=6.15 Hz), 1.51–2.12 (m, 6H), 3.23–3.25 (m, 1H), 3.46–3.50 (m, 4H), 3.62 (br s, 1H), 4.77 (s, 1H), 5.55–5.63 (m, 2H), 7.35–7.38 (m, 1H), 7.44–7.48 (m, 1H).

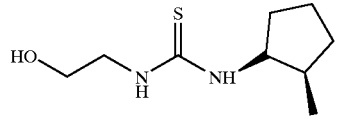

1-(2-Hydroxy-ethyl)-3-(cis-2-methyl-cyclopentyl)-thiourea (Compound 12)

The title compound was obtained (10.55g, 49%) from commercially available trans-2-methylcyclopentanol according to General Procedure D. Spectroscopic data: $^1$H NMR (D$_6$ DMSO, 300 MHz) δ 7.35 (s, 1H), 7.32 (s, 1H), 4.75 (br s, 1H), 4.49 (br s, 1H), 3.45 (br s, 4H), 2.18–1.98 (m, 1H), 1.91–1.56 (m, 3H), 1.49–1.34 (m, 2H), 1.27–1.17 (m, 1H), 0.79 (d, J=6.74 Hz, 3H).

General Procedure C for the preparation of cycloalkyl hydroxyethyl thioureas:

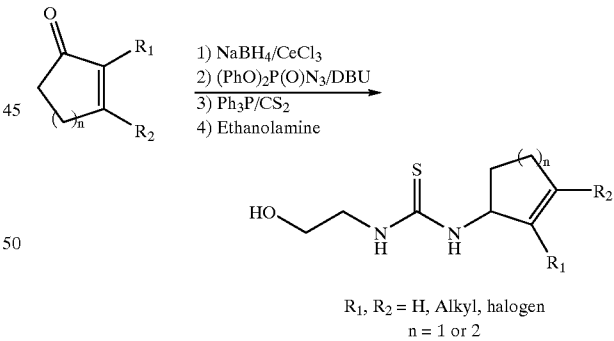

$R_1, R_2$ = H, Alkyl, halogen
n = 1 or 2

Sodium borohydride (1 eq) was added to a mixture of the respective enone and of cerium trichloride heptahydrate (1 eq) in methanol at 0° C. The resulting reaction mixture was stirred at 0° C. for 30 minutes. The reaction mixture was then diluted with water and extracted with ether. The combined organic phases were washed with water and brine, and then dried (MgSO$_4$) and concentrated to give a crude allylic alcohol, which was dissolved in toluene, and treated with diphenylphosphoryl azide (1.1 eq) and 1,8-diazabicyclo (5.4.0)undec-7-ene (DBU 1.1 eq) for 3 hours at room temperature. Concentration and chromatography gave the allylic azide, which was dissolved in carbon disulphide, and treated with triphenyl phosphine (1.1 eq). The reaction mixture was refluxed for 4 hours, then concentrated and diluted with pentane. The solids formed were washed with pentane. The combined pentane layers were concentrated to yield the crude isothiocyanate, which was dissolved immediately in acetonitrile, and treated with ethanolamine (6 mL) and catalytic amount of dimethylaminopyridine for 14 hours at room temperature. Concentration, followed by chromatography (50% EtOAc:hexanes to 10% MeOH/EtOAc) afforded the final product.

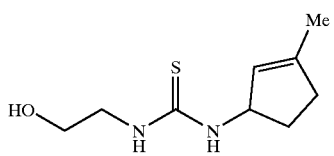

1-(2-Hydroxy-ethyl)-3-(3-methyl-cyclopent-2-enyl)-thiourea (Compound 13)

The title compound was obtained (5.02 g, 40%) from the commercially available 3-methyl-2,3-cyclopenten-1-one (5.00 g) according to General Procedure C. Spectroscopic data: $^1$H NMR (D$_6$ DMSO, 300 MHz) δ=7.45 (d, J=7.62 Hz, 1H), 7.22 (br s, 1H), 5.32 (s, 1H), 5.12 (br s, 1H), 4.73 (br s, 1H), 3.44 (br s, 4H), 2.35–2.04 (m, 3H), 1.71 (s, 3H), 1.63–1.46 (m, 1H).

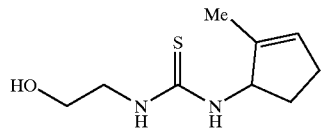

1-(2-Hydroxy-ethyl)-3-(2-methyl-cyclopent-2-enyl)-thiourea (Compound 14)

The title compound was obtained (6.21 g, 60%) from commercially available 2-methyl-2,3-cyclopenten-1-one (5.00 g) according to General Procedure C. Spectroscopic data: $^1$H NMR (D$_6$ DMSO, 300 MHz) δ 7.50 (d, J=8.21 Hz, 1H), 7.28 (br s, 1H), 5.48 (s, 1H), 5.16 (br s, 1H), 4.76 (br s, 1H), 3.46 (br s, 4H), 2.36–2.07 (m, 3H), 1.63 (s, 3H), 1.54–1.33 (m, 1H).

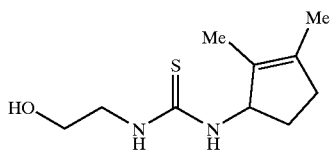

1-(2,3-Dimethyl-cyclopent-2-enyl)-3-(2-hydroxy-ethyl)-thiourea (Compound 15)

The title compound was obtained (2.67 g, 27%) from commercially available 2,3-dimethyl-2,3-cyclopenten-1-one (5.00 g) according to General Procedure C. Spectroscopic data: $^1$H NMR (D$_6$ DMSO, 300 MHz) δ 7.43 (d, J=6.74 Hz, 1H), 7.25 (br s, 1H), 5.17 (br s, 1H), 4.76 (br s, 1H), 3.46 (br s, 4H), 2.36–1.99 (m, 3H), 1.62 (s, 3H), 1.1.54 (s, 3H), 1.47–1.22 (m, 1H).

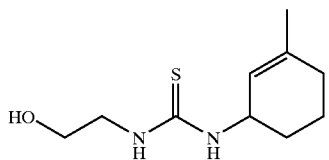

1-(2-Hydroxy-ethyl)-3-(3-methyl-cyclohex-2-enyl)-thiourea (Compound 16)

The title compound was generated from commercially available 3-methylcyclohex-2-enone according to General Procedure C. Spectroscopic data: $^1$H NMR (D$_6$ DMSO, 300 MHz) δ 1.38–1.74 (m, 6H), 1.84–1.90 (m, 2H), 1.98 (s, 1H), 3.45–3.47 (m, 4H), 4.75 (s, 2H), 5.32 (s, 1H), 7.25 (s, 1H), 7.43 (d, 1H, J=7.91 Hz).

General Procedure E for the Synthesis of 1-(2-halo-cyclohex-1-enylmethyl)-3-(2-hydroxy-ethyl)-thiourea:

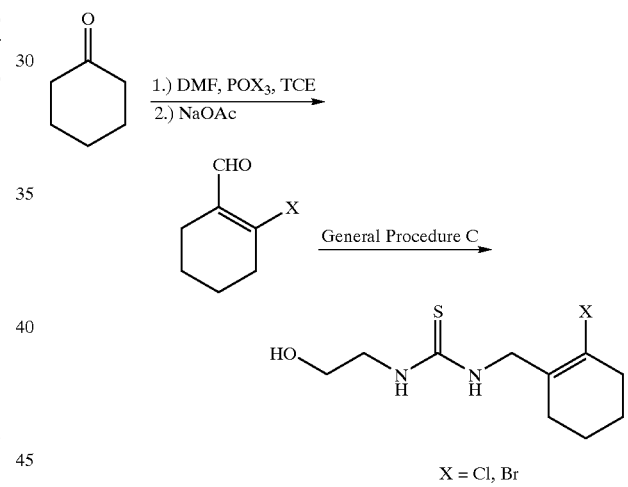

X = Cl, Br

Phosphorous oxyhalide (4.9 mL, 1 eq) was added dropwise to a solution of dimethylformamide (6.3 mL, 1.4 eq) in 16 mL of trichloroethylene at 0° C. The reaction mixture was allowed to warm to room temperature slowly, after which commercially available cyclohexanone (6 mL, 58 mmol) dissolved in 16 mL of trichloroethylene was added dropwise. The mixture was warmed to 60° C. for 3 hours. It was then cooled to 0° C. and NaOAc (40 g, 8.4 eq) dissolved in 56 mL of water was added slowly. The mixture was stirred at room temperature overnight and extracted with CH$_2$Cl$_2$. The organic layer was washed with H$_2$O (100 mL, 3×), brine and dried over MgSO$_4$. The mixture was then concentrated on the rotary evaporator and treated once more with NaOAc (400 mg, anhydrous). The NaOAc was filtered and washed with MeOH. The filtrate was concentrated to give the crude aldehyde, which was converted to the final thiourea as described in General Procedure C.

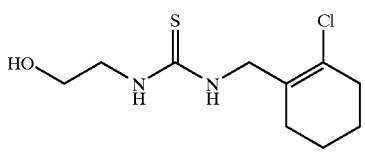

1-(2-chloro-cyclohex-1-enylmethyl)-3-(2-hydroxy-ethyl)thiourea (Compound 17)

Commercially available cyclohexanone was converted to (2-chlorocyclohex-1-enyl)carboxaldehyde according to General Procedure E. Sodium borohydride/cerium chloride reduction of the above carboxaldehyde, in accordance with the method described in General Procedure C gave the intermediate (2-chlorocyclohex-1-enyl)-methanol in 46% yield, which was characterized: $^1$H NMR (CDCl$_3$, 300 MHz) δ=1.61–1.75 (m, 4H), 2.15 (br s, 1H), 2.22–2.27 (m, 2H), 2.33–2.37 (m, 2H), 4.24 (br s, 2H). The title compound was obtained from (2-chloro-cyclohex-1-enyl)methanol according to General Procedure C. Spectroscopic data: $^1$H NMR (D$_6$ DMSO, 300 MHz) δ=1.52–1.69 (m, 4H), 2.07–2.11 (m, 2H), 2.28–2.35 (m, 2H), 3.48 (br s, 4H), 4.22 (br s, 2H), 4.76 (s, 1H), 7.41 (s, 1H), 7.54 (s, 1H).

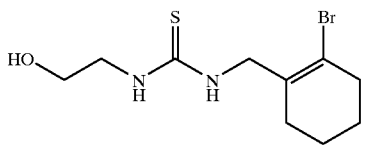

1-(2-Bromo-cyclohex-1-enylmethyl)-3-(2-hydroxy-ethyl)-thiourea (Compound 18)

Cyclohexanone (6.0 mL, 58 mmol) and phosphorous oxybromide (5.9 mL, 1 eq) were treated as described in General Procedure E to give 1.57 g of the intermediate (2-bromocyclohex-1-enyl)carboxaldehyde. This aldehyde was converted to the title compound according to General Procedure C. Spectroscopic data: $^1$H NMR (D$_6$ DMSO, 300 MHz) δ=1.57–1.67 (m, 4H), 2.09–2.11 (m, 2H), 2.45–2.51 (m, 2H), 3.46–3.48 (m, 4H), 4.19 (br s, 2H), 4.77 (s, 1H), 7.44 (s, 1H), 7.57 (s, 1H).

General Procedure F for the Synthesis of 1-(2-hydroxyethyl)-substituted-cyclohex-2-enylmethyl)-thioureas:

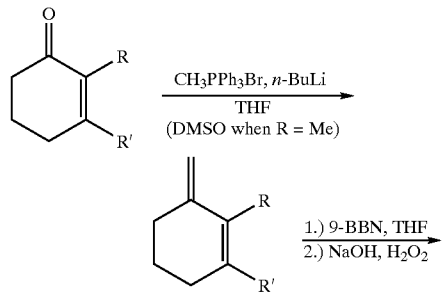

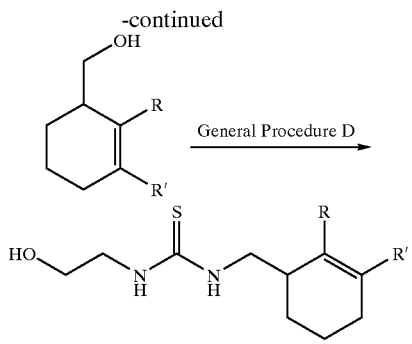

R and R' H or alkyl n-BuLi (1.2 eq) was added slowly to a solution of methyltriphenylphosphonium bromide (1.2 eq) in 25 mL of THF at −78° C. The resulting mixture was stirred for 30 minutes and then allowed to warm to room temperature for 1 hour. The reaction was cooled to −78° C. and the respective substituted cyclohex-2-enone (1 eq, some available commercially) dissolved in 10 mL of THF was added slowly. After 30 minutes, the reaction was allowed to slowly warm to room temperature. The reaction was quenched with saturated NH$_4$Cl and extracted with Et$_2$O (20 mL 3x). The combined organic extracts were washed with H$_2$O (20 mL, 3x), brine and dried over MgSO$_4$. The mixture was concentrated and the resulting residue purified by column chromatography using CH$_2$Cl$_2$ as eluant to give the desired diene. The diene was dissolved in THF, and 9-borabicyclo(3.3.1)nonane (9-BBN, 1 eq) was added slowly at 0° C. After 5 hours 1M NaOH was added slowly to basify the reaction mixture. 500 μL of 30% H$_2$O$_2$ was added slowly and the resulting mixture extracted with Et$_2$O (10 mL 3x). The combined organic extracts were washed with H$_2$O (5 mL, 3x), brine and dried over MgSO$_4$. Purification by column chromatography using CH$_2$Cl$_2$ as eluant gave the desired substituted cyclohex-2-enyl)methanol, which was then converted to the desired hydroxyethyl thiourea described in General Procedure D. Some of the commercially unavailable starting enones were prepared according to the processes disclosed below.

General Synthesis of C-3 substituted cyclohex-2-enones:

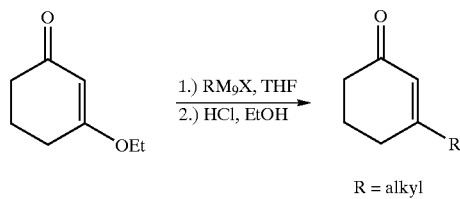

R = alkyl

3-Ethyl-cyclohex-2-enone

Ethyl magnesium chloride (8.6 mL, 1.2 eq) was added dropwise to a solution of commercially available 3-ethoxy-2-cyclohexenone (2.0 g, 14.3 mmol) in 50 mL THF at 0° C. After 30 minutes 1M HCl was added and stirring continued for 1 hour. The mixture was extracted with ether and the combined organic extracts were washed with H$_2$O (25 mL, 3x), brine and dried over MgSO$_4$. The mixture was then concentrated and the resulting residue purified by column chromatography using EtOAc/hex (2:1) as eluant to give a quantitative yield of the title enone. Spectroscopic data: $^1$H NMR (CDCl$_3$, 300 MHz) δ=1.11 (t, 3H, J=7.20 Hz), 1.95–2.04 (m, 2H), 2.21–2.38 (m, 6H), 5.87 (s, 1H).

General Synthesis of C-2 substituted cyclohex-2-enones:

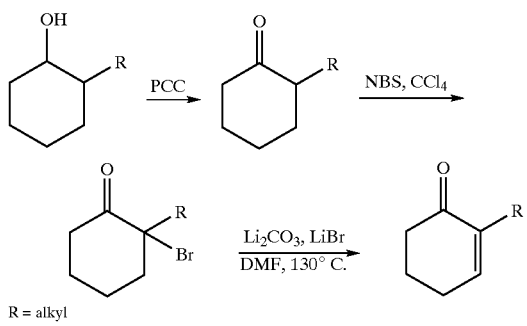

R = alkyl

Synthesis of 2,3-Dimethyl-cyclohex-2-enone

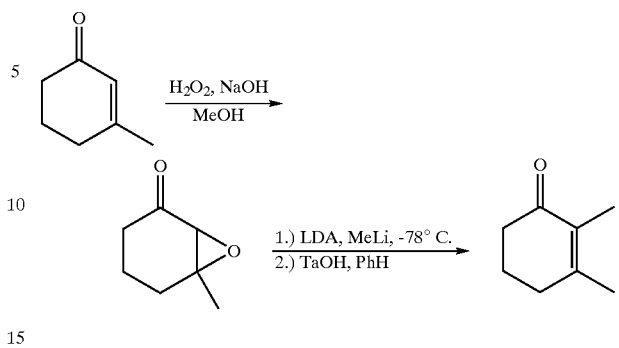

2-Ethyl-cyclohexanone

Celite (25 g) and pyridinium chlorochromate (PCC, 25 g, 1.5 eq, 0.12 moles) were added consecutively to a solution of commercially available 2-ethylcyclohexanol (10 g, 78 mmol) in 300 mL $CH_2Cl_2$. The resulting reaction mixture was stirred at room temperature for 1 hour after which it was filtered and concentrated on the rotary evaporator. The residue was purified by column chromatography using EtOAc/hex (1:2) as eluant to give 7.57 g (77%) of the title ketone. Spectroscopic data: $^1$H NMR ($CDCl_3$, 300 MHz) δ=0.89 (t, 3H, J=7.47 Hz), 1.18–1.45 (m, 2H), 1.63–1.89 (m, 4H), 1.99–2.42 (m, 5H).

2-Methyl-cyclohex-2-enone

Commercially available 2-methylcyclohexanone (10 g, 89 mmol) and N-bromo succinimid (NBS 15.87 g, 1 eq) were refluxed in 200 mL of $CCl_4$ for overnight. The resulting reaction mixture was filtered through celite and concentrated on the rotary evaporator. The residue was dissolved in DMF (100 mL). $Li_2CO_3$ (10 g, 135 mmol) and LiBr (12.13 g, 140 mole) were added. The resulting mixture was then heated to 130° C. for 3 hours. After cooling to room temperature the reaction was extracted with $Et_2O$ (100 mL 3x). The combined organic extracts were washed with $H_2O$ (50 mL, 3x), brine and dried over $MgSO_4$. The mixture was concentrated on the rotary evaporator and the resulting residue was purified by column chromatography using EtOAc/hex (1:3) as eluant to give 3.77 g (74%) of the title compound. Spectroscopic data: $^1$H NMR ($CDCl_3$, 300 MHz) δ=1.76–1.79 (m, 3H), 1.95–2.03 (m, 2H), 2.30–2.36 (m, 2H), 2.40–2.45 (m, 2H), 6.73–6.77 (m, 1H).

2-Ethyl-cyclohex-2-enone

Following the procedure utilized for the preparation of 2-methyl-cyclohex-2-enone 6.6 g (89% yield) of the title compound was obtained from 2-ethylcyclohexanone (7.57 g, 60 mmole). Spectroscopic data: $^1$H NMR ($CDCl_3$, 300 MHz) δ=1.01 (t, 3H, J=7.48 Hz), 1.94–2.02 (m, 2H), 2.17–2.25 (m, 2H), 2.32–2.45 (m, 4H), 6.70–6.72 (m, 1H).

A solution of commercially available 3-methyl-cyclohex-2-enone (10 g, 90.78 mmol) in MeOH was cooled to 0° C. $H_2O_2$ (27.8 mL, 3 eq) was added dropwise followed by NaOH (635 μL, 0.035 eq). The resulting mixture was stirred for 2.5 hours and then quenched with cold saturated NaCl. Extraction with $CH_2Cl_2$ followed by concentration and purification by column chromatography using EtOAc/hex (1:3) gave 7.67 g (67% yield) of the desired keto epoxide. Spectroscopic data: $^1$H NMR ($CDCl_3$, 300 MHz) δ=1.46 (s, 3H), 1.62–1.69 (m, 1H), 1.83–2.16 (m, 4H), 2.45–2.53 (m, 1H), 3.07 (s, 1H). A solution of this keto epoxide (8.91 g, 70 mmol) in 71 mL THF was added to a solution of lithium diisopropylamine (LDA 56.5 mL, 1.2 eq) in 85 mL of THF at −78° C. The reaction mixture was stirred for 30 minutes, and MeLi (121 mL, 2.4 eq) was added slowly. The temperature was brought up to −23° C. and the reaction was stirred for 2 hours. The reaction was quenched with saturated $NH_4Cl$ and the resulting solution was extracted with EtOAc. The combined organic extracts were washed with water, brine, and dried over $MgSO_4$. Concentration followed by column chromatography afforded the alcohol intermediate, which was dissolved in benzene and refluxed with toluenesulfonic (2.2 g, 11.6 mmol) for 15 minutes. The reaction was diluted with EtOAc, washed with water, brine, and dried over $MgSO_4$. Concentration followed by column chromatography using EtOAc/hex (1:4) as eluant gave 1.17 g (13.5%) of the title compound. Spectroscopic data: $^1$H NMR ($CDCl_3$, 300 MHz) δ=1.77 (br s, 3H), 1.89–1.99 (m, 5H), 2.32–2.40 (m, 4H).

Synthesis of 2-propylcyclohex-2-enone

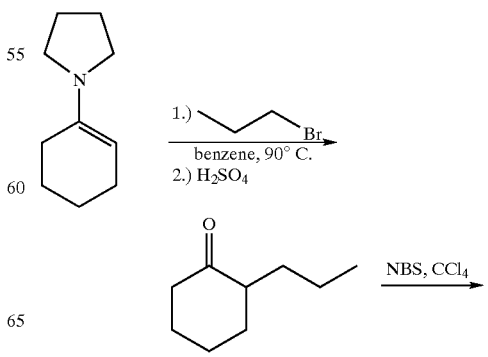

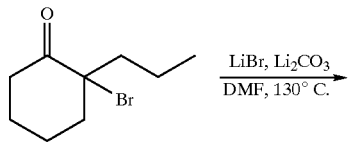

A solution of commercially available 1-cyclohex-1-enylpyrrolidine 1(5 g, 99.2 mmol) and propyl bromide (36 mL, 4 eq) in benzene was refluxed at 90° C. for overnight. Another 4 eq of propyl bromide (36 mL) was added and refluxing was continued for overnight. The reaction mixture was cooled to room temperature. 30 mL of water was added, and the resulting solution refluxed for 1 hour. After cooling to room temperature, 30 mL of 1M $H_2SO_4$ was added and the solution stirred for 10 minutes. The mixture was extracted with ether, and the combined organic extracts were washed with $NaHCO_3$, $H_2O$, brine, and dried over $MgSO_4$. Purification by column chromatography using EtOAc/hex (1:3) as eluant afforded 2.12 g (15.3%) of 2-propylcyclohexanone. Spectroscopic data: $^1H$ NMR ($CDCl_3$, 300 MHz) δ=0.90 (t, 3H, J=7.035 Hz), 1.14–1.45 (m, 5H), 1.63–1.88 (m, 4H), 1.99–2.14 (m, 2H), 2.23–2.42 (m, 2H).

2-propylcyclohexanone was converted to the title compound (1.16 g, 55% yield) following the general procedure described above for the synthesis of 2-substituted cyclohe-2-enones. Spectroscopic data: $^1H$ NMR ($CDCl_3$, 300 MHz) δ=0.89 (t, 3H, J=7.325 Hz), 1.35–1.45 (m, 3H), 1.93–2.02 (m, 2H), 2.13–2.18 (m, 2H), 2.32–2.38 (m, 3H), 6.70 (t, 1H, J=4.25 Hz).

Synthesis of 2-Bromocyclohex-2-enone

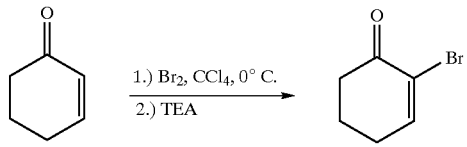

A solution of $Br_2$ in $CCl_4$ (2.7 mL, 101 eq) was added slowly to a solution of commercially available cyclohex-2-enone (5 g, 52 mmol) in $CCl_4$ cooled to 0° C. The reaction was stirred for 20 minutes, after which a solution of triethylamine (TEA 13 mL, 1.8 eq) in $CCl_4$ (5mL) was added slowly. Stirring was continued for 2 hours. The resulting mixture was diluted with $CH_2Cl_2$, washed with $H_2O$, brine, and dried over $MgSO_4$. Purification by column chromatography using $CH_2Cl_2$/hex (1:4) as eluant afforded 6.75 g (74.2%) of the title compound. Spectroscopic data: $^1H$ NMR ($CDCl_3$, 300 MHz) δ=2.04–2.13 (m, 2H), 2.44–2.49 (m, 2H), 2.62–2.66 (m, 2H), 7.43 (t, J=4.55 Hz, 1H).

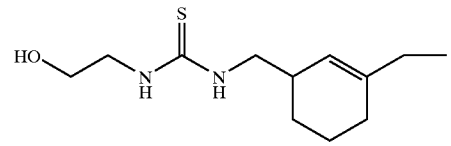

1-(2-Hydroxy-ethyl)-3-(3-ethyl-cyclohex-2-enylmethyl)-thiourea (Compound 19)

The title compound was made from 3-ethylcyclohex-2-enone (prepared previously) according to General Procedure F. The intermediates 3-methylene-1-ethyl-cyclohexene, (3-ethyl-cyclohex-2-enyl)-methanol, 3-azidomethyl-1-ethyl-cyclohexene and the isothiocyanate 1-ethyl-3-isothiocyanatomethyl-cyclohexene were isolated and characterized as follows:

3-Methylene-1-ethyl-cyclohexene: Spectroscopic data: $^1H$ NMR ($CDCl_3$, 300 MHz) δ=1.04 (t, 3H, J=7.47 Hz), 1.64–1.74 (m, 2H), 1.99–2.10 (m, 4H), 2.26–2.31 (m, 2H), 4.665 (d, 2H, J=8.79 Hz), 5.93 (s, 1H).

(3-Ethyl-cyclohex-2-enyl)-methanol: Spectroscopic data: $^1H$ NMR ($CDCl_3$, 300 MHz) δ=0.99 (t, 3H, J=7.565 Hz), 1.50–1.60 (m, 2H), 1.71–1.77 (m, 2H), 1.92–1.99 (m, 5H), 2.28 (br s, 1H), 3.505 (d, 2H, J=6.35 Hz), 5,28 (br s, 1H).

3-Azidomethyl-1-ethyl-cyclohexene: Spectroscopic data: $^1H$ NMR ($CDCl_3$, 300 MHz) δ=0.99 (t, 3H, J=7.475 Hz), 1.50–1.59 (m, 2H), 1.70–1.79 (m, 2H), 1.91–2.00 (m, 4H), 2.35 (br s, 1H), 3.175 (d, 2H, J=6.4 Hz), 5.26 (br s, 1H).

1-Ethyl-3-isothiocyanatomethyl-cyclohexene: Spectroscopic data: $^1H$ NMR ($CDCl_3$, 300 MHz) δ=1.00 (t, 3H, J=7.325 Hz), 1.71–1.84 (m, 3H), 1.93–2.02 (m, 5H), 2.48 (br s, 1H), 3.385 (d, 2H, J=6.45 Hz), 5.22 (br s, 1H).

1-(3-Ethyl-cyclohex-2-enylmethyl)-3-(2-hydroxy-ethyl)-thiourea: Spectroscopic data: $^1H$ NMR ($D_6$ DMSO, 300 MHz) δ=0.093 (t, 3H, J=7.5 Hz), 1.17 (t, 2H, J=7.5 Hz), 1.38–1.47 (m, 1H), 1.61–1.71 (m, 2H), 1.86–1.93 (m, 3H), 2.29 (br s, 1H), 3.33 (br s, 2H), 3.43–3.47 (m, 4H), 4.75 (br s, 1H), 5.25 (br s, 1H), 7.37 (br s, 1H), 7.54 (br s, 1H).

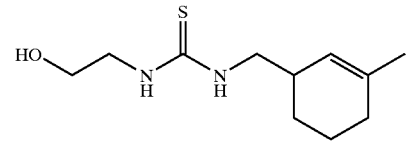

1-(2-Hydroxy-ethyl)-3-(3-methyl-cyclohex-2-enylmethyl)-thiourea (Compound 20)

The title compound was made from commercially available 3-methylcyclohex-2-enone according to General Procedure F. The intermediates 3-methylene-1-methyl-cyclohexene, (3-methyl-cyclohex-2-enyl)-methanol, methanesulfonic acid 3-methyl-cyclohex-2-enylmethyl ester, 3-azidomethyl-1-methyl-cyclohexene and the isothiocyanate 1-methyl-3-isothiocyanatomethyl-cyclohexene were isolated and characterized as follows:

1-Methyl-3-methylene-cyclohexene: Spectroscopic data: $^1H$ NMR ($CDCl_3$, 300 MHz) δ=1.66–1.75 (m, 5H), 2.00–2.04 (m, 2H), 2.25–2.30 (m, 2H), 4.64 (d, 2H), 5.93 (s, 1H).

(3-Ethyl-cyclohex-2-enyl)-methanol: Spectroscopic data: ¹H NMR (CDCl₃, 300 MHz) δ=1.26–1.90 (m, 10H), 2.26 (br s, 1H), 3.50 (d, 2H, J=6.0 Hz), 5.30 (br s, 1H).

Methanesulfonic acid 3-ethyl-cyclohex-2-enylmethyl ester: Spectroscopic data: ¹H NMR (CDCl₃, 300 MHz) δ=1.28–1.92 (m, 9H), 2.51 (br s, 1H), 3.01 (s, 3H), 4.045 (d, 2H, J=9.0 Hz), 5.25 (br s, 1H).

3-Azidomethyl-1-ethyl-cyclohexene: Spectroscopic data: ¹H NMR (CDCl₃, 300 MHz) δ=1.27–1.83 (m, 7H), 1.97 (br s, 2H), 2.39 (br s, 1H), 3.22–3.24 (m, 2H), 5.32 (br s, 1H).

1-Ethyl-3-isothiocyanatomethyl-cyclohexene: Spectroscopic data: ¹H NMR (CDCl₃, 300 MHz) δ=1.25–1.36 (m, 2H), 1.49–1.85 (m, 5H), 1.90–1.96 (m, 2H), 2.46 (br s, 1H), 3.38 (d, 2H, J=6.44 Hz), 5.23 (br s, 1H).

1-(2-Hydroxy-ethyl)-3-(3-methyl-cyclohex-2-enylmethyl)-thiourea: Spectroscopic data: ¹H NMR (D₆ DMSO, 300 MHz) δ=1.12–1.18 (m, 1H), 1.40–1.46 (m, 1H), 1.62–1.71 (m, 5H), 1.81–1.90 (m, 2H), 2.28 (br s, 1H), 3.26–3.32 (m, 2H), 3.42–3.47 (m, 4H), 4.76 (br s, 1H), 5.26 (br s, 1H), 7.37 (br s, 1H), 7.53 (br s, 1H).

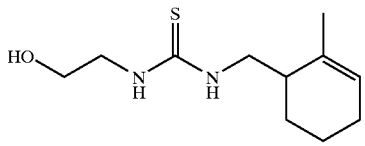

1-(2-Hydroxy-ethyl)-3-(2-methyl-cyclohex-2-enylmethyl)-thiourea (Compound 21)

The title compound was prepared from 2-methylcyclohex-2-enone (prepared previously) according to the General Procedure F. The intermediates (2-methyl-cyclohex-2-enyl)-methanol, methanesulfonic acid 2-methyl-cyclohex-2-enylmethyl ester, 2-azidomethyl-1-methyl-cyclohexene and the isothiocyanate 1-methyl-2-isothiocyanatomethyl-cyclohexene were isolated and characterized as follows:

(2-Methyl-cyclohex-2-enyl)-methanol: Spectroscopic data: ¹H NMR (CDCl₃, 300 MHz) δ=1.39–1.98 (m, 10H), 2.16 (br s, 1H), 3.64–3.73 (in, 2H), 5.57 (br s, 1H).

Methanesulfonic acid 2-methyl-cyclohex-2-enylmethyl ester: Spectroscopic data: ¹H NMR (CDCl₃, 300 MHz) δ=1.55–1.75 (m, 7H), 1.97–2.02 (m, 2H), 2.39 (br s, 1H), 3.02 (s, 3H), 4.11–4.31 (m, 2H), 5.58 (br s, 1H).

2-Azidomethyl-1-methyl-cyclohexene: Spectroscopic data: ¹H NMR (CDCl₃, 300 MHz) δ=1.49–1.72 (m, 7H), 1.94–2.01 (m, 2H), 2.20 (br s, 1H), 3.22–3.29 (m, 1H), 3.43–3.48 (m, 1H), 5.53–5.55 (m, 1H).

1-Methyl-2-isothiocyanatomethyl-cyclohexene: Spectroscopic data: ¹H NMR (CDCl₃, 300 MHz) δ=1.50–1.80 (m, 7H), 1.96–2.02 (m, 2H), 2.33 (br s, 1H), 3.54–3.58 (m, 2H), 5.56–5.61 (m, 1H).

1-(2-Hydroxy-ethyl)-3-(2-methyl-cyclohex-2-enylmethyl)-thiourea: Spectroscopic data: ¹H NMR (D₆ DMSO, 300 MHz) δ=1.41–1.62 (m, 4H), 1.67 (s, 3H), 1.92 (br s, 2H), 2.19 (br s, 1H), 3.20 (br s, 1H), 3.47 (br s, 4H), 3.70 (br s, 1H), 4.79 (s, 1H), 5.44 (s, 1H), 7.41 (s, 1H), 7.48 (s, 1H).

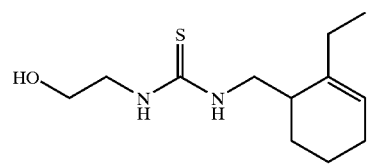

1-(2-Hydroxy-ethyl)-3-(2-ethyl-cyclohex-2-enylmethyl)-thiourea (Compound 22)

The title compound was generated from 2-ethylcyclohex-2-enone (prepared previously) according to General Procedure F. The intermediates 1-methyl-3-methylene-cyclohexene, (2-ethyl-cyclohex-2-enyl)-methanol, methanesulfonic acid 2-ethyl-cyclohex-2-enylmethyl ester, 2-azidomethyl-1-ethyl-cyclohexene and the isothiocyanate 1-ethyl-2-isothiocyanatomethyl-cyclohexene were isolated and characterized as follows:

1-Ethyl-3-methylene-cyclohexene: Spectroscopic data: ¹H NMR (CDCl₃, 300 MHz) δ=1.06 (t, 3H, J=7.33 Hz), 1.62–1.72 (m, 2H), 2.12–2.25 (m, 4H), 2.32–2.37 (m, 2H), 4.74 (s, 1H), 4.91 (s, 1H), 5.67 (br s, 1H).

(2-Ethyl-cyclohex-2-enyl)-methanol: Spectroscopic data: ¹H NMR (CDCl₃, 300 MHz) δ=1.01 (t, 3H, J=7.33 Hz), 1.50–1.70 (m, 5H), 1.97–2.06 (m, 4H), 2.25 (br s, 1H), 3.62–3.67 (m, 2H), 5.56 (br s, 1H).

Methanesulfonic acid 2-ethyl-cyclohex-2-enylmethyl ester: Spectroscopic data: ¹H NMR (CDCl₃, 300 MHz) δ=1.02 (t, 3H, J=7.33 Hz), 1.56–1.81 (m, 4H), 1.99–2.06 (m, 4H), 2.49 (br s, 1H), 3.02 (s, 3H), 4.09–4.15 (m, 1H), 4.25–4.30 (m, 1H), 5.58 (br s, 1H).

2-Azidomethyl-1-ethyl-cyclohexene: Spectroscopic data: ¹H NMR (CDCl₃, 300 MHz) δ=1.01 (t, 3H, J=7.33 Hz), 1.52–1.74 (m, 4H), 1.97–2.03 (m, 4H), 2.28 (br s, 1H), 3.19–3.26 (m, 1H), 3.41–3.46 (m, 1H), 5.53–5.54 (m, 1H).

1-Ethyl-2-isothiocyanatomethyl-cyclohexene: Spectroscopic data: ¹H NMR (CDCl₃, 300 MHz) δ=1.01 (t, 3H, J=7.475 Hz), 1.51–1.65 (m, 2H), 1.70–1.77 (m, 2H), 1.92–2.05 (m, 4H), 2.39–2.43 (m, 1H), 3.51–3.56 (m, 2H), 5.57–5.60 (m, 1H).

1-(2-Hydroxy-ethyl)-3-(2-ethyl-cyclohex-2-enylmethyl)-thiourea: Spectroscopic data: ¹H NMR (D₆ DMSO, 300 MHz) δ=0.98 (t, 3H, J=7.33 Hz), 1.43–1.61 (m, 4H), 1.94–2.06 (m, 4H), 2.30 (s, 1H), 3.09–3.19 (m, 1H), 3.47 (br s, 4H), 3.72 (br s, 1H), 4.78 (s, 1H), 5.44 (s, 1H), 7.39 (s, 1H), 7.51 (s, 1H).

General Procedure G for the synthesis of 1-(2-Hydroxy-ethyl)-3-(2-alkyl-cycloalk-1-enylmethyl)-thiourea:

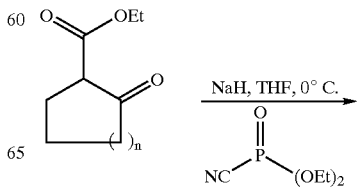

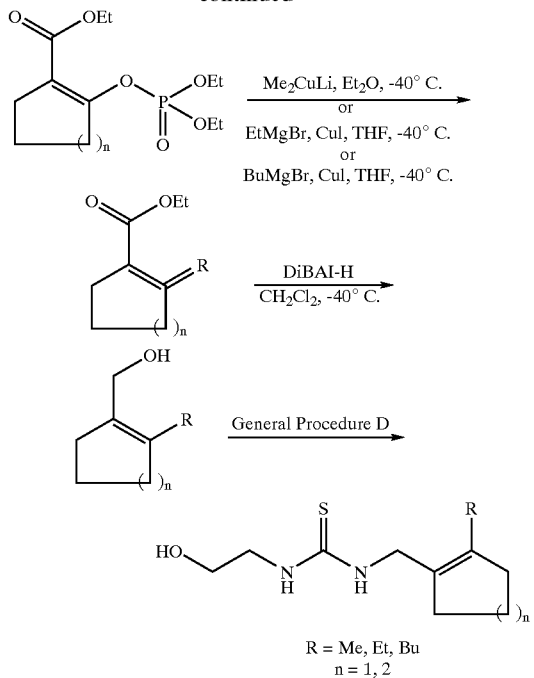

A solution of NaH (2 eq) in 30 mL THF was cooled to 0° C. Commercially available ethyl-2-cyclohexanonecarboxylate dissolved in 10 mL THF was added slowly and the resulting mixture was stirred for 45 minutes. Diethyl cyanophosphonate (1.01 eq) was added, and after 1 hour the reaction was quenched with water. The mixture was extracted with EtOAc (3×100 mL) and the combined organic extracts were washed with $H_2O$ (25 mL, 3×) and brine and dried over $MgSO_4$. The mixture was concentrated on the rotary evaporator to give the virtually pure phosphono ester derivative shown in the scheme above. In another reaction vessel, MeLi (2–3 eq) was added dropwise to a suspension of CuI (1 eq) in ether (60 mL) at 0° C. The resulting solution was immediately cooled to −40° C., and the phosphono ester prepared previously (1 eq) in 20 mL of ether was added. The reaction was stirred for 2 hours at −40° C., after which it was allowed to slowly warm to room temperature. Saturated $NH_4Cl$ containing 10% $NH_4OH$ was added to quench the reaction. Filtration followed by concentration of the filtrate gave a residue which was purified by column chromatography to give the desired unsaturated ester. Di-iso-butyl aluminum hydride (DiBA1H-H 2 eq) was added to a solution of the unsaturated ester in $CH_2Cl_2$ cooled to −40° C. The resulting reaction mixture was stirred for 2.5 hours and then allowed to slowly come to room temperature. The reaction was quenched with water, filtered through celite and the filtrate concentrated. The residue was purified by column chromatography using EtOAc/hex (1:3) as eluant, to give the desired alcohol, which was converted to the final thiourea using in accordance with General Procedure D.

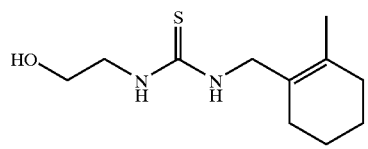

1-(2-Hydroxy-ethyl)-3-(2-methyl-cyclohex-1-enylmethyl)-thiourea (Compound 23)

The title compound was prepared from commercially available ethyl 2-oxocyclohexanecarboxylate according to General Procedure G. The intermediates 2-(diethoxy-phosphoryloxy)-cyclohex-1-enecarboxylic acid ethyl ester, 2-methyl-cyclohex-1-enecarboxylic acid ethyl ester, (2-methyl-cyclohex-1-enyl)-methanol, methanesulfonic acid 2-methyl-cyclohex-1-enylmethyl ester, 1-azidomethyl-2-methyl-cyclohexene and the isothiocyanate 1-isothiocyanatomethyl-2-methyl-cyclohexene were isolated and characterized as follows:

2-(Diethoxy-phosphoryloxy)-cyclohex-1-enecarboxylic acid ethyl ester: Spectroscopic data: $^1H$ NMR ($CDCl_3$, 300 MHz) δ=1.26–1.38 (m, 9H), 1.59–1.76 (m, 4H), 2.33–2.39 (m, 2H), 2.43–2.49 (m, 2H), 4.13–4.25 (m, 6H).

2-Methyl-cyclohex-1-enecarboxylic acid ethyl ester: Spectroscopic data: $^1H$ NMR ($CDCl_3$, 300 MHz) δ=1.29 (t, 3H, J=7.18 Hz), 1.58–1.62 (m, 4H), 1.98 (s, 3H), 2.11 (br s, 2H), 2.26 (br s, 2H), 4.11–4.22 (m, 2H).

(2-Methyl-cyclohex-1-enyl)-methanol: Spectroscopic data: $^1H$ NMR ($CDCl_3$, 300 MHz) δ=1.57–1.69 (m, 8H), 1.96 (br s, 2H), 2.10 (br s, 2H), 4.10 (s, 2H), Methanesulfonic acid 2-methyl-cyclohex-1-enylmethyl ester: Spectroscopic data: $^1H$ NMR ($CDCl_3$, 300 MHz) δ=1.55–1.64 (m, 4H), 1.73 (s, 3H), 2.00 (br s, 2H), 2.12 (br s, 2H), 4.09 (s, 2H).

1-Azidomethyl-2-methyl-cyclohexene: Spectroscopic data: $^1H$ NMR ($CDCl_3$, 300 MHz) δ=1.57–1.65 (m, 4H), 1.71 (s, 3H), 2.02–2.04 (m, 4H), 3.77 (s, 2H).

1-Isothiocyanatomethyl-2-methyl-cyclohexene: Spectroscopic data: $^1H$ NMR ($CDCl_3$, 300 MHz) δ=1.55–1.68 (m, 7H), 1.98–2.07 (m, 4H), 4.08 (s, 2H).

1-(2-Hydroxy-ethyl)-3-(2-methyl-cyclohex-1-enylmethyl)-thiourea: Spectroscopic data: $^1H$ NMR ($D_6$ DMSO, 300 MHz) δ=1.51 (br s, 4H), 1.64 (s, 3H), 1.91–1.98 (m, 4H), 3.45–3.47 (m, 4H), 3.98 (br s, 2H), 4.76 (s, 1H), 7.28 (s, 1H), 7.36 (s, 1H).

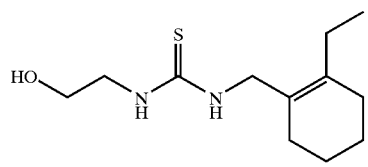

1-(2-Hydroxy-ethyl)-3-(2-ethyl-cyclohex-1-enylmethyl)-thiourea (Compound 24)

The title compound was prepared from commercially available ethyl 2-oxocyclohexanecarboxylate according to the General Procedure G. The intermediates 2-ethylcyclohex-1-enecarboxylic acid ethyl ester and (2-ethyl-cyclohex-1-enyl)-methanol, were isolated and characterized as follows:

2-Ethyl-cyclohex-1-enecarboxylic acid ethyl ester: Spectroscopic data: $^1$H NMR (CDCl$_3$, 300 MHz) δ=0.97–1.07 (m, 2H), 1.22–1.32 (m, 3H), 1.58–1.68 (m, 4H), 2.12–2.36 (m, 7H), 4.09–4.21 (m, 2H).

(2-Ethyl-cyclohex-1-enyl)-methanol: Spectroscopic data: $^1$H NMR (CDCl$_3$, 300 MHz) δ=0.97 (t, 3H, J=7.47 Hz), 1.58–1.68 (m, 5H), 2.00–2.11 (m, 5H), 4.09 (m, 2H).

1-(2-Hydroxy-ethyl)-3-(2-ethyl-cyclohex-1-enylmethyl)-thiourea: Spectroscopic data: $^1$H NMR (D$_6$, DMSO, 300 MHz) δ=0.93 (t, 3H, J=7.61 Hz), 1.51–1.53 (m, 4H), 1.95–2.06 (m, 6H), 3.46 (br s, 4H), 3.99 (br s, 2H), 4.74 (s, 1H), 7.34 (br s, 2H).

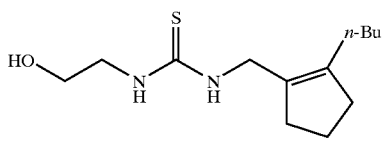

1-(2-Butyl-cyclopent-1-enylmethyl)-3-(2-hydroxyethyl)-thiourea (Compound 25)

The title compound was prepared from commercially available methyl 2-oxocyclopentanecarboxylate according to General Procedure G. The intermediates 2-butyl-cyclopent-1-enecarboxylic acid methyl ester and 1-azidomethyl-2-butyl-cyclopentene were isolated and characterized as follows: 2-Butyl-cyclopent-1-enecarboxylic acid methyl ester: 10 g of the corresponding phosphono ester gave 2.59 g (40%) of the title compound. Spectroscopic data: $^1$H NMR (CDCl$_3$, 300 MHz) δ 3.71 (s, 3H), 2.68–2.57 (m, 4H), 2.49 (t, J=7.03 Hz, 2H), 1.88–1.73 (m, 2H), 1.49–1.25 (m, 4H), 0.92 (t, J=7.33 Hz, 3H).

1-Azidomethyl-2-butyl-cyclopentene: Spectroscopic data: $^1$H NMR (CDCl$_3$, 300MHz) δ 3.83 (s, 2H), 2.46–2.36 (m, 4H), 2.12 (t, J=7.03 Hz, 2H), 1.90–1.80 (m, 2H), 1.43–1.24 (m, 4H), 0.91 (t, J=7.33 Hz, 3H).

1-(2-Butyl-cyclopent-1-enylmethyl)-3 -(2-hydroxyethyl)-thiourea: 0.43 g of the title compound was obtained, 35% based on the isolated intermediate (2-butyl-cyclopent-1-enyl)-methanol. Spectroscopic data: $^1$H NMR (CDCl$_3$, 300 MHz) δ 7.39 (br s, 1H), 7.33 (br s, 1H), 4.78 (br s, 1H), 4.06 (br s, 2H), 3.46 (br s, 4H), 2.29 (br s, 4H), 2.09 (t, J=7.03 Hz, 2H), 1.72 (quintet, J=7.03 Hz, 2H), 1.38–1.17 (m, 4H), 0.87 (t, J=7.33 Hz, 3H).

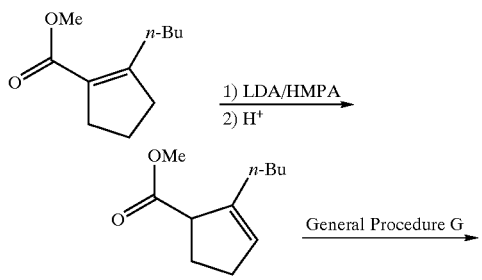

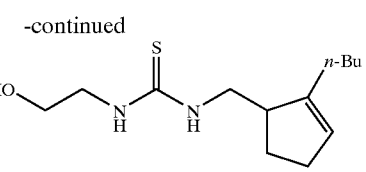

1-(2-Butyl-cyclopent-2-enylmethyl)-3-(2-hydroxyethyl)-thiourea (Compound 26)

n-BuLi (1.5 eq) was added to diisopropylamine (1.8 eq) and hexamethylphosphoramide (HLMPA 5 mL) in THF (20 mL) at 0° C. After 10 minutes, the reaction mixture was cooled to −78° C., and 2-butyl-cyclopent-1-enecarboxylic acid methyl ester (prepared as described in Genereal Procedure G) was added. The resulting reaction mixture was stirred at −78° C. for 60 minutes and then quenched with dilute HCl (2N, 20 mL). The mixture was extracted with ether and the combined ether layers were washed with water, brine, then concentrated. The resulting crude ester was converted to the final thiourea in accordance with General Procedure G.

1-(2-Butyl-cyclopent-2-enylmethyl)-3-(2-hydroxyethyl)-thiourea: 0.74 g of the title compound was obtained, 60% based on the isolated intermediate (2-butyl-cyclopent-2-enyl)-methanol. Spectroscopic data: $^1$H NMR (CDCl$_3$, 300 MHz) δ 7.42 (br s, 1H), 7.33 (br s, 1H), 5.38 (br s, 1H), 3.50–3.35 (m, 4H), 3.10 (br s, 1H), 2.72 (br s, 1H), 2.31–1.85 (m, 4H), 1.80–1.50 (m, 1H), 1.48–1.20 (m, 3H), 0.88 (t, J=7.33 Hz, 3H).

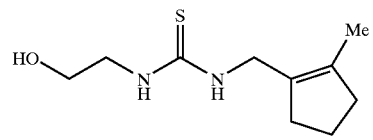

1-(2-Methyl-cyclopent-1-enylmethyl)-3-(2-hydroxyethyl)-thiourea (Compound 27)

The title compound was prepared from methyl 2-oxocyclopentanecarboxylate according to General Procedure G. The intermediate (2-methyl-cyclopent-1-enyl)-methanol was isolated and characterized as follows:

(2-Methyl-cyclopent-1-enyl)-methanol. Spectroscopic data: $^1$H NMR (CDCl$_3$, 300 MHz) δ 4.19 (s, 2H), 2.45 (t, J=6.45 Hz, 2H), 2.33 (t, J=7.03 Hz, 2H), 1.81 (quintet, J=7.62 Hz, 2H), 1.69 (s, 3H).

1-(2-Methyl-cyclopent-1-enylmethyl)-3-(2-hydroxyethyl)-thiourea: Spectroscopic data: $^1$H NMR (CDCl$_3$, 300 MHz) δ 6.47 (br s, 1H), 4.03 (br s, 2H), 3.85–3.78 (m, 4H), 3.68 (br s, 1H), 2.42–2.29 (m, 3H), 2.18 (s, 3H), 1.91–1.72 (m, 4H).

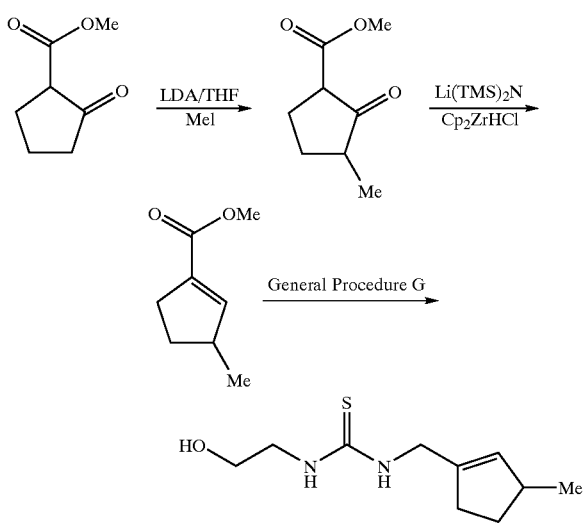

1-(2-Hydroxy-ethyl)-3-(3-methyl-cyclopent-1-enylmethyl)-thiourea (Compound 28)

The intermediate 3-methyl-cyclopent-1-enecarboxylic acid methyl ester was prepared as described below: n-BuLi (40.00 mL, 2.5 M in hexane, 100.00 mmol) was added to diisopropylamine (15.00 mL) in THF at 0° C. After 10 minutes, commercially available methyl 2-oxocyclopentanecarboxylate was added. The reaction mixture was stirred at 0° C. for another 10 minutes, then methyl iodide was added. The resulting reaction mixture was allowed to warm to room temperature over 20 minutes, then quenched with 2N HCl (50 mL). The mixture was extracted with ether, and the combined ether layers were washed with brine, then dried over magnesium sulfate and concentrated. 5.43 g of the methylated ester was dissolved in ethylene glycol dimethyl ether (DME) and cooled to −78° C., then Li(TMS)$_2$N (42.00 mL, 1.0 M in THF, 42.00 mmol) was added. After 60 minutes, the reaction mixture was transferred to Cp$_2$ZrHCl in DME at 0° C. Stirring was continued for another 60 minutes and then the reaction mixture was concentrated. Chromatography (5% EtOAc/hex) gave 1.40 g (29%) of 3-methyl-cyclopent-1-enecarboxylic acid methyl ester. This ester was converted to the final thiourea in accordance with General Procedure G. The intermediates 3-methyl-cyclopent-1-enecarboxylic acid methyl ester and 1-azidomethyl-3-methyl-cyclopentene were isolated and characterized as follows:

3-Methyl-cyclopent-1-enecarboxylic acid methyl ester: Spectroscopic data: $^1$H NMR (CDCl$_3$, 300 MHz) δ 6.66 (br s, 1H), 3.74 (s, 3H), 2.98–2.80 (m, 1H), 2.68–2.45 (m, 2H), 2.25–2.11 (m, 1H), 1.54–1.42 (m, 1H), 1.09 (d, J=7.03 Hz, 3H).

1-Azidomethyl-3-methyl-cyclopentene: Spectroscopic data: $^1$H NMR (CDCl$_3$, 300 MHz) δ 5.60 (br s, 1H), 3.81 (s, 2H), 2.87–2.73 (m, 1H), 2.43–2.28 (m, 2H), 2.24–2.11 (m, 1H), 1.51–1.39 (m, 1H), 1.03 (d, J=7.03 Hz, 3H).

1-(2-Hydroxy-ethyl)-3-(3-methyl-cyclopent-1-enylmethyl)-thiourea: 1.12 g (52%) of the title compound was obtained. The yield was based on intermediate 3-methyl-cyclopent-1-enecarboxylic acid methyl ester.

Spectroscopic data: $^1$H NMR (D$_6$ DMSO, 300 MHz) δ 7.57 (br s, 1H), 7.43 (br s, 1H), 5.40 (br s, 1H), 4.79 (br s, 1H), 4.06 (br s, 2H), 3.49–3.37 (m, 4H), 2.71–2.69 (m, 1H), 2.35–2.02 (m, 4H), 0.97 (d, J=6.74 Hz, 3H).

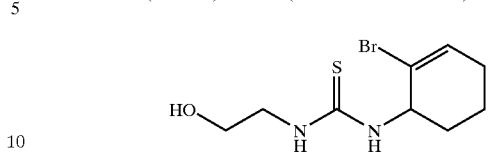

1-(2-Bromo-cyclohex-2-enyl)-3-(2-Hydroxy-ethyl)-thiourea (Compound 29)

The title compound was prepared from 2-bromocyclohex-2-enone (prepared previously) according to General Procedure C. The intermediates 2-bromo-cyclohex-2-enol, 6-azido-1-bromo-cyclohexene, and the isothiocyanate 1-bromo-6-isothiocyanato-cyclohexene were isolated and characterized as follows:

2-Bromo-cyclohex-2-enol: The crude allylic alcohol was chromatographed using EtOAc/hex (1:3) as eluant to afford 6.34 g (93%) of pure 2-bromocyclohex-2-enol. Spectroscopic data: $^1$H NMR (CDCl$_3$, 300 MHz) δ 1.57–1.81 (m, 2H), 1.90–2.21 (m, 4H), 2.40 (br s, 1H), 4.19–4.23 (m, 1H), 6.20 (t, 1H, J=4.11 Hz).

6-Azido-1-bromo-cyclohexene: The crude azide was chromatographed to afford 5.36 g of pure 6-azido-1-bromocyclohexene (74% yield). Spectroscopic data: $^1$H NMR (CDCl$_3$, 300 MHz) δ 1.66–1.73 (m, 2H), 1.94–2.21 (m, 4H), 3.99–4.02 (m, 1H), 6.33 (t, 1H, J=4.1 Hz).

1-Bromo-6-isothiocyanato-cyclohexene: 5.10 g (88% yield). Spectroscopic data: $^1$H NMR (CDCl$_3$, 300 MHz) δ 1.69–1.78 (m, 2H), 1.90–2.20 (m, 4H), 4.33–4.37 (m, 1H), 6.27–6.30 (m, 1H).

1-(2-Bromo-cyclohex-2-enyl)-3-(2-hydroxy-ethyl)thiourea. Spectroscopic data: $^1$H NMR (D$_6$ DMSO, 300 MHz) δ 1.47–1.63 (m, 2H), 1.78–1.81 (m, 2H), 1.98–2.15 (m, 2H), 3.48 (br s, 4H), 4.78 (s, 1H), 4.98 (s, 1H), 6.25 (t, 1H), J=3.665 Hz), 7.38 (s, 1H), 7.825 (d, 1H, J=8.79 Hz).

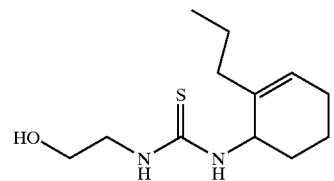

1-(2-Hydroxy-ethyl)-3-(2-propyl-cyclohex-2-enyl)-thiourea (Compound 30)

The title compound was prepared from 2-propylcyclohex-2-enone (prepared previously) according to General Procedure C. The intermediate 2-propylcyclohex-2-enol was isolated and characterized as follows:

2-propylcyclohex-2-enol: Following General Procedure C, 1.16 g (8.39 mmol) of the starting 2-propylcyclohex-2-enone afforded 840 mg (71% yield) of the desired enol. Spectroscopic data: $^1$H NMR (CDCl$_3$, 300 MHz) δ 0.91 (t, 3H, J=7.325 Hz), 1.33–1.80 (m, 8H), 1.95–2.05 (m, 3H), 4.06 (br s, 1H), 5.54 (br s, 1H).

1-(2-Hydroxy-ethyl)-3-(2-propyl-cyclohex-2-enyl) thiourea Spectroscopic data: $^1$H NMR (D$_6$ DMSO, 300 MHz) δ 0.82 (t, 3H, J=7.325 Hz), 1.26–1.66 (m, 5H), 1.76–2.03 (m, 5H), 3.47 (br s, 4H), 4.78 (br s, 2H), 5.54 (s, 1H), 7.30 (s, 1H), 7.485 (d, 1H, J=8.79 Hz).

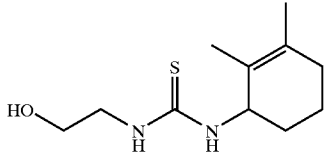

1-(2,3-Dimethyl-cyclohex-2-enyl)-3-(2-hydroxy-ethyl)-thiourea (Compound 31)

The title compound was prepared from 2,3-dimethylcyclohex-2-enone (prepared previously) according to General Procedure C. The intermediate 2,3-dimethylcyclohex-2-enol was isolated and characterized as follows:

2,3-Dimethylcycolohex-2-enol: 1.58 g (12.74 mmol) of 2,3-dimethylcyclohex-2-enone afforded 930 mg (58%) of the desired alcohol. Spectroscopic data: $^1$H NMR (CDCl$_3$, 300 MHz) δ 1.56–1.74 (m, 11H), 1.93 (br s, 2H), 3.95 (br s, 1H).

1-(2,3-Dimethyl-cyclohex-2-enyl)-3-(2-hydroxy-ethyl)-thiourea: Spectroscopic data: $^1$H NMR (D$_6$ DMSO, 300 MHz) δ 1.50–1.66 (m, 10H), 1.90 (br s, 2H), 3.46 (br s, 4H), 4.64 (s, 1H), 4.76 (s, 1H), 7.24 (s, 1H), 7.525 (d, 1H, J=8.21 Hz).

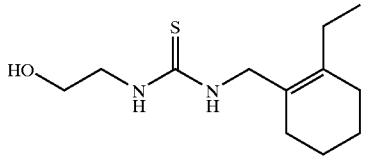

1-(2-Hydroxy-ethyl)-3-(3-ethyl-cyclohex-2-enyl)-thiourea (Compound 32)

The title compound was prepared from 3-ethylcyclohex-2-enone (prepared previously) according to the General Procedure C. The intermediate 3-ethylcyclohex-2-enol was isolated and characterized as follows:

3-Ethylcyclohex-2-enol: Following General Procedure C, 3.91 g (31.5 mmol) of the starting 3-ethylcyclohex-2-enone afforded 2.61 g (66% yield) of the desired alcohol. Spectroscopic data: $^1$H NMR (CDCl$_3$) δ=1.01 (t, 3H, J=7.475 Hz), 1.54–1.63 (m, 2H), 1.71–1.81 (m, 2H), 1.90–2.02 (m, 5H), 4.19 (br s, 1H), 5.49 (br s, 1H).

1-(2-Hydroxy-ethyl)-3-(3-ethyl-cyclohex-2-enyl)-thiourea: Spectroscopic data: $^1$H NMR (D$_6$ DMSO, 300 MHz) δ 0.96 (t, 3H, J=7.325 Hz), 1.40–1.78 (m, 4H), 1.91–1.99 (m, 4H), 3.46 (br s, 4H), 4.76 (br s, 2H), 5.32 (s, 1H), 7.27 (s, 1H), 7.45 (d, 1H, J=8.21 Hz).

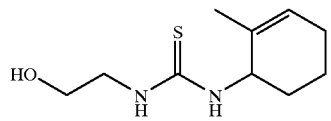

1-(2-Hydroxy-ethyl)-3-(2-methyl-cyclohex-2-enyl)-thiourea (Compound 33)

The title compound was prepared from 2-methylcyclohex-2-enone (prepared previously) according to General Procedure C. The intermediate 2-methylcyclohex-2-enol was isolated and characterized as follows:

2-Methylcyclohex-2-enol: Following General Procedure C, 6.65 g (60.4 mmol) of the starting 2-methylcyclohex-2-enone afforded 5.56 g (82% yield) of the desired alcohol. Spectroscopic data: $^1$H NMR (CDCl$_3$, 300 MHz) δ 1.54–2.02 (m, 10H), 3.98 (br s, 1H), 5.53 (br s, 1H).

1-(2-Hydroxy-ethyl)-3-(2-methyl-cyclohex-2-enyl)-thiourea: Spectroscopic data: $^1$H NMR (D$_6$ DMSO, 300 MHz) δ 1.45–1.525 (m, 2H), 1.60–1.65 (m, 5H), 1.90–1.98 (m, 2H), 3.46 (br s, 4H), 4.70 (s, 1H), 4.78 (s, 1H), 5.53 (s, 1H), 7.30 (s, 1H), 7.50 (d, 1H, J=8.50 Hz).

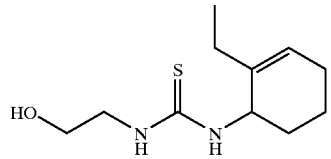

1-(2-Hydroxy-ethyl)-3-(2-ethyl-cyclohex-2-enyl)-thiourea (Compound 34)

The title compound was prepared from 2-ethylcyclohex-2-enone (prepared previously) according to General Procedure C. Spectroscopic data: $^1$H NMR (D$_6$ DMSO, 300 MHz) δ 0.95 (t, 3H, J=7.475 Hz), 1.52–1.66 (m, 4H), 1.91–1.98 (m, 4H), 3.47 (br, s, 4H), 4.79 (br s, 2H), 5.54 (s, 1H), 7.30 (s, 1H), 7.495 (d, 1H, J=8.49 Hz).

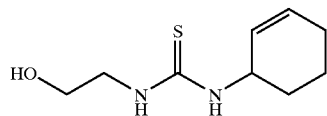

1-(Cyclohex-2-enyl)-3-(2-hydroxy-ethyl)-thiourea (Compound 35)

The title compound was prepared from 2-ethylcyclohex-2-enone (prepared previously) according to the General Procedure C. Spectroscopic data: $^1$H NMR (D$_6$ DMSO, 300 MHz) δ 1.43–1.60 (m, 3H), 1.77–1.84 (m, 1H), 1.91–2.04 (m, 2H), 3.46 (br s, 4H), 4.78 (br s, 2H), 5.58–5.61 (m, 1H), 5.78–5.82 (m, 1H), 7.32 (s, 1H), 7.495 (d, 1H, J=7.92 Hz).

General Procedure H for the synthesis of cis substituted cyclohexanols:

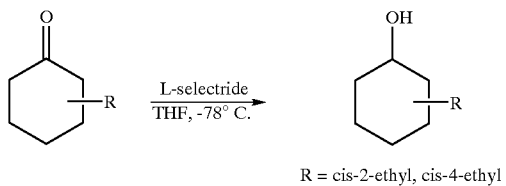

R = cis-2-ethyl, cis-4-ethyl

The commercially available reagent lithium tri-sec-butylborohydride (L-Selectride 1.2 eq) was added to a solution of substituted cyclohexanone in THF at −78° C. After stirring for 1 hour, the reaction was warmed to 0° C., and 5N NaOH was added to basify the reaction mixture, followed by 10 mL of $H_2O_2$. The reaction mixture was extracted with $Et_2O$, and the combined organic extracts were washed with $H_2O$, brine, and dried over $MgSO_4$. Purification by column chromatography gave the desired cis alcohol.

cis-2-Ethyl-cyclohexanol: The title compound was obtained as described in General Procedure H. Chromatography using EtOAc/hex (1:3) as eluant afforded 1.5 g (20% yield) of the title compound. Spectroscopic data: $^1$H NMR ($CDCl_3$, 300 MHz) δ 0.91 (t, 3H, J=7.035 Hz), 1.17–1.68 (m, 11H), 1.74–1.84 (m, 1H), 3.90 (br s, 1H).

cis-4-Ethylcyclohexanol: Following General Procedure H, 3.0 g (23.77 mmol) of 4-ethylcyclohexanol afforded 2.13 g (69.6% yield) of the title compound. Spectroscopic data: $^1$H NMR ($CDCl_3$, 300 MHz) δ 0.88 (t, 3H, J=7.18 Hz), 1.16–1.59 (m, 10H), 1.65–1.76 (m, 2H), 3.91–3.96 (m, 1H).

General Procedure I for the synthesis of trans-substituted cyclohexyl hydroxyethyl thioureas:

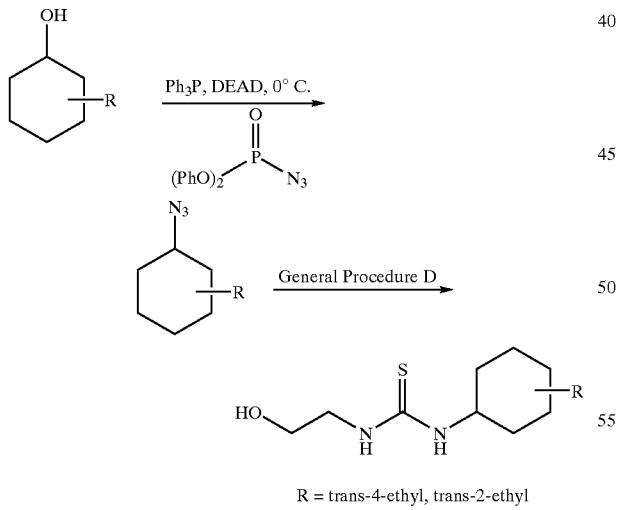

R = trans-4-ethyl, trans-2-ethyl

To a solution of the substituted cyclohexanols (prepared as described above in accordance with General Procedure H) in THF at 0° C. was added triphenylphosphine (1 eq) followed by commercially available diethylazodicarboxylate (DEAD 1 eq). The resulting reaction mixture was stirred overnight. The solvent was evaporated and the residue was extracted with hexane. The combined extracts were concentrated to give the crude azide, which was converted to the final thiourea following General Procedure D.

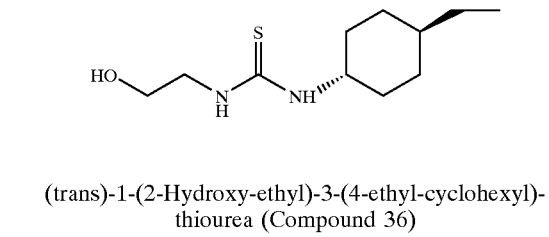

(trans)-1-(2-Hydroxy-ethyl)-3-(4-ethyl-cyclohexyl)-thiourea (Compound 36)

The title compound was obtained from cis-4-ethylcyclohexanol (prepared in accordance with General Procedure H) according to General Procedure I. Spectroscopic data: $^1$H NMR ($D_6$ DMSO, 300 MHz) δ=0.83 (t, 3H, J=7.56 Hz), 0.88–0.94 (m 2H), 1.04–1.21 (m, 5H), 1.69–1.72 (m, 2H), 1.89–1.91 (m, 2H), 3.41–3.46 (m, 4H), 3.87 (br s, 1H), 4.73 (s, 1H), 7.19 (s, 1H), 7.325 (d, 1H, J=8.30 Hz).

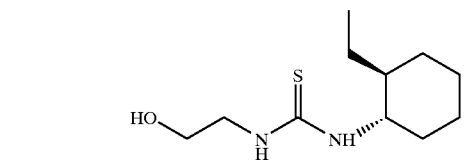

1-(trans-2-Ethyl-cyclohexyl)-3-(2-hydroxy-ethyl)-thiourea (Compound 37)

The title compound was obtained from cis-2-ethylcyclohexanol (prepared in accordance with General Procedure H) according to General Procedure I. Spectroscopic data: $^1$H NMR ($D_6$ DMSO, 300 MHz) δ 0.81 (t, 3H, J=7.18 Hz), 0.95–1.24 (m, 6H), 1.46–1.93 (m, 5H), 3.47 (br s, 4H), 3.89 (br s, 1H), 4.77 (s, 1H), 7.19 (s, 1H), 7.325 (d, 1H, J=8.5 Hz).

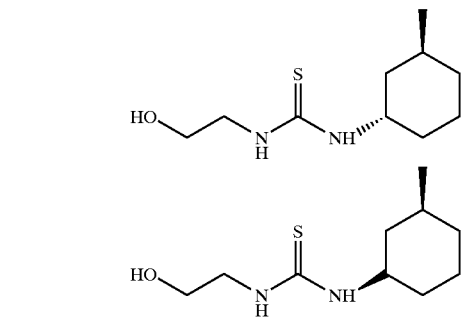

cis-and trans-1-(2-Hydroxy-ethyl)-3-(3-methyl-cyclohexyl)-thioureas (Compounds 38 and 39)

The title compounds were obtained from the commercially available 3-methylcyclohexanol (presumably a mixture of cis and trans isomers) according to General Procedure I. The isomers were separated using column chromatography. The structural assignment of isomerism was based on the synthesis of the trans isomer from cis-3-methylcyclohexanol using General Procedure I. Spectroscopic data for both compounds are as follows:

(trans)-1-(2-Hydroxy-ethyl)-3-(3-methyl-cyclohexyl)-thiourea: $^1$H NMR (D$_6$ DMSO, 300 MHz) δ 0.87 (d, 3H, J=5.86 Hz), 0.95–1.01 (m, 1H), 1.15–1.24 (m, 1H), 1.42–1.63 (m, 7H), 3.46–3.49 (m, 4H), 4.37 (s, 1H), 4.79 (s, 1H), 7.41 (s, 1H), 7.53 (s, 1H).

(cis)-1-(2-Hydroxy-ethyl)-3-(3-methyl-cyclohexyl)-thiourea: $^1$H NMR (D$_6$ DMSO, 300 MHz) δ 0.72–0.83 (m, 2H), 0.87 (d, 3H, J=6.45 Hz), 0.95–1.0 (m, 1H), 1.22–1.29 (m, 1H), 1.38–1.42 (m, 1H), 1.56–1.65 (m, 1H), 1.61–1.71 (m, 1H), 1.86–1.90 (m, 2H), 3.45–3.47 (m, 4H), 3.92 (br s, 1H), 4.76 (s, 1H), 7.21 (s, 1H), 7.33 (d, 1H, J=7.91 Hz).

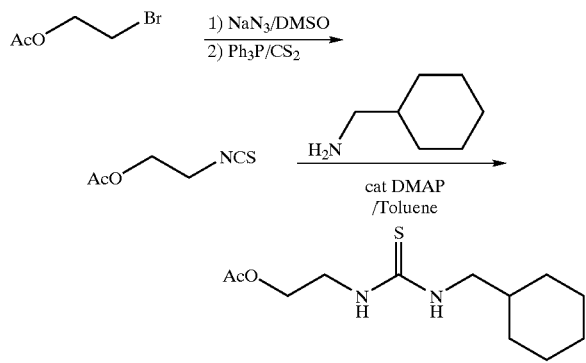

Acetic Acid 2-(3-Cyclohexylmethyl-thioureido)-ethyl Ester (Compound 42)

Acetic acid 2-bromo-ethyl ester (15.00 g, 89.81 mmol) and sodium azide (11.68 g, 179.63 mmol) was mixed in DMSO (200 mL) at room temperature and the resulting reaction mixture was stirred at the same temperature for 14 hours, then diluted with water. The mixture was extracted with ether, and the combined organic phases were washed with water and brine, then dried over magnesium sulfate and concentrated to give quantitative yield of the desired azide. Spectroscopic data: $^1$H NMR (CDCl$_3$, 300 MHz) δ 4.23 (t, J=5.50 Hz, 2H), 3.46 (t, J=5.50 Hz, 2H), 2.10 (s, 3H). 3g of this azide was then mixed with triphenylphosphine (1 eq) in carbon disulfide and the mixture was stirred at room temperature for 14 hours. After concentration, the reaction mixture was diluted with pentane. The solids formed were washed with more pentane, and the combined pentane layers were concentrated to afford the desired isothiocyanate. This isothiocyanate was then mixed with cyclohexanemethylamine (5.00 mL, 38.47 mmol) in toluene, followed by the addition of catalytic amount of DMAP (20 mg). The resulting reaction mixture was stirred at room temperature for 14 hours, then concentrated. Chromatography (gradient solvent system, from 50% EtOAc/Hexanes to 10% MeOH/EtOAc) gave 3.02 g (57%) of the desired product. Spectroscopic data: $^1$H NMR (D$_6$ DMSO, 300 MHz) δ 7.45 (br s, 1H), 7.35 (t, J=4.50 Hz, 1H), 4.08 (t, J=5.40 Hz, 2H), 3.64 (br s, 2H), 3.20 (br s, 2H), 2.00 (s, 3H).

What is claimed is:

1. A compound in accordance with formula (i) or formula (ii)

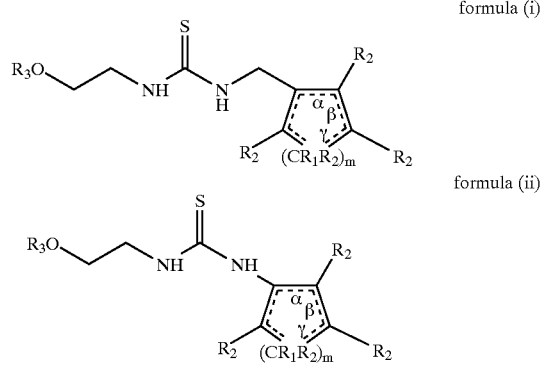

wherein the dotted line represents a bond, or absence of a bond with the provisos that only one dotted line represents a bond in the ring of formula (i) or of formula (ii);

R$_1$ is H, or is absent when the carbon bearing the R$_1$ is double bonded;

R$_2$ is H, alkyl of 1 to 4 carbons, alkenyl of 2 to 4 carbons, alkynyl of 2 to 4 carbons; OH, O-alkyl where the alkyl group has 1 to 4 carbons, OCOR$_4$ where R$_4$ is alkyl of 1 to 4 carbons, F, Cl, Br or I;

m is an integer having the values of 1, 2 or 3 with the proviso that when the compound is in accordance with formula (i) and m is 2 then the dotted line designated γ represents absence of a bond, and R$_3$ is H, or R$_4$CO, with the further provisos that when the compound is in accordance with formula (ii) then R$_2$ is not OH, and when the compound is in accordance with formula (ii) and m is 1 then at least one R$_2$ of the five-membered ring is not H.

2. A compound in accordance with claim 1 where m is 1.

3. A compound in accordance with claim 2 having the structure in accordance with formula (i).

4. A compound in accordance with claim 3 wherein R$_2$ is H, alkyl of 1 to 4 carbons, Cl, or Br.

5. A compound in accordance with claim 2 having the structure in accordance with formula (ii).

6. A compound in accordance with claim 5 wherein R$_2$ is H, alkyl of 1 to 4 carbons, Cl, or Br.

7. A compound in accordance with claim 1 where m is 2.

8. A compound in accordance with claim 7 having the structure in accordance with formula (i).

9. A compound in accordance with claim 8 wherein R$_2$ is H, alkyl of 1 to 4 carbons, Cl, or Br.

10. A compound in accordance with claim 7 having the structure in accordance with formula (ii).

11. A compound in accordance with claim 10 wherein R$_2$ is H, alkyl of 1 to 4 carbons, Cl, or Br.

12. A pharmaceutical composition for treating such diseases or conditions of a mammal which are responsive to treatment by agonists of α$_{2B}$ or α$_{2C}$ adrenergic receptors, the composition containing an effective amount of one or more compounds in accordance with claim 1 and a pharmaceutically acceptable excipient.

13. A compound of the formula

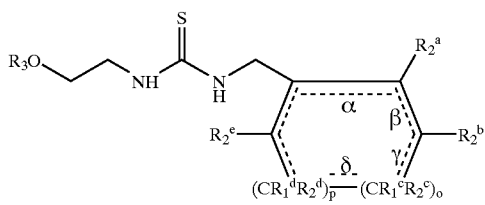

wherein each dotted line represents a bond, or the absence of a bond, with the proviso that only one dotted line represents a bond;

$R_1^c$ is H or does not exist when the adjacent carbon is double bonded;

$R_1^d$ is H or does not exist when the adjacent carbon is double bonded or when p is 0;

$R_2^a$ is H, alkyl of 1 to 4 carbons, F, Cl, Br or I;

$R_2^b$ is H or alkyl of 1 to 4 carbons;

$R_2^c$ is H or alkyl of 1 to 4 carbons;

$R_2^d$ is H or does not exist when p is 0;

$R_2^e$ is H or alkyl of 1 to 4 carbons.

$R_3$ is H or $COCH_3$; o is an integer having the values 1 or 2, and p is an integer having the values 0 or 1.

14. A compound in accordance with claim 13 where o is 1 and p is 1.

15. A compound in accordance with claim 14 where the dotted line β represents a double bond.

16. A compound in accordance with claim 15 selected from the group consisting of compounds where:

(1) $R_2^a$ is H, $R_2^b$ is ethyl, $R_2^c$, $R_1^c$, $R_2^d$, $R_1^d$, $R_2^e$ and $R_3$ are H;

(2) $R_2^a$ is H, $R_2^b$ is methyl and $R_2^c$, $R_1c$, $R_2^d$, $R_1^d$, $R_2^e$ and $R_3$ are H;

(3) $R_2^a$, $R_2^b$, $R_2^c$, $R_1^c$, $R_2^d$, $R_1^d$, $R_2^e$ and $R_3$ are H;

(4) $R_2^a$ is methyl and $R_2^b$, $R_2^c$, $R_1^c$, $R_2^d$, $R_1^d$, $R_2^e$ and $R_3$ are H, and (4) $R_2^a$ is ethyl and $R_2^b$, $R_2^c$, $R_1c$, $R_2^d$, $R_1^d$, $R_2^e$ and $R_3$ are H.

17. A compound in accordance with claim 14 where no dotted line represents a bond.

18. A compound in accordance with claim 17 selected from the groups consisting of compounds where:

(1) $R_2^a$, $R_2^b$, $R_2^c$, $R_1^c$, $R_2^d$, $R_1^d$, $R_2^e$ and $R_3$ are H, and (2) $R_2^a$, $R_2^b$, $R_2^c$, $R_1^c$, $R_2^d$, $R_1^d$ and $R_2^e$ are H and $R_3$ is $CH_3CO$.

19. A compound in accordance with claim 14 where the dotted line δ represents a double bond.

20. A compound in accordance with claim 19 selected from the groups consisting of compounds where:

(1) $R_2^a$, $R_2^b$, $R_2^c$, $R_2^d$, $R_2^e$ and $R_3$ are H, and (2) $R_2^a$ is methyl and $R_2^b$, $R_2^c$, $R_2^d$, $R_2^e$ and $R_3$ are H.

21. A compound in accordance with claim 14 where the dotted line α represents a double bond.

22. A compound in accordance with claim 21 selected from the groups consisting of compounds where:

(1) $R_2^a$, $R_2^b$, $R_2^c$, $R_1^c$, $R_2^d$, $R_1^d$, $R_2^e$ and $R_3$ are H;

(2) $R_2^a$ is methyl and $R_2^b$, $R_2^c$, $R_1^c$, $R_2^d$, $R_1^d$, $R_2^e$ and $R_3$ are H;

(3) $R_2^a$ is methyl and $R_2^b$, $R_2^c$, $R_1^c$, $R_2^d$, $R_1^d$, $R_2^e$ and $R_3$ are H;

(4) $R_2^a$ is Cl and $R_2^b$, $R_2^c$, $R_1^c$, $R_2^d$, $R_1^d$, $R_2^e$ and $R_3$ are H, and (2) $R_2^a$ is Br and $R_2^b$, $R_2^c$, $R_1^c$, $R_2^d$, $R_1^d$, $R_2^e$ and $R_3$ are H.

23. A compound in accordance with claim 14 where the dotted line γ represents a double bond.

24. A compound in accordance with claim 13 where o is 2 and p is 1.

25. A compound in accordance with claim 24 where no dotted line represents a bond and $R_2^a$, $R_2^b$, $R_2^c$, $R_1^c$, $R_2^d$, $R_1^d$, $R_2^e$ and $R_3$ are H.

26. A compound in accordance with claim 13 where o is 1 and p is 0.

27. A compound in accordance with claim 26 where no dotted line represents a bond and $R_2^a$, $R_2^b$, $R_2^c$, $R_1^c$, $R_2^e$ and $R_3$ are H.

28. A compound in accordance with claim 26 where the dotted line β represents a double bond.

29. A compound in accordance with claim 28 where $R_2^a$ is n-butyl, and $R_2^b$, $R_2^c$, $R_1^c$, $R_2^e$ and $R_3$ are H.

30. A compound in accordance with claim 26 where the dotted line α represents a double bond.

31. A compound in accordance with claim 30 selected from the groups consisting of compounds where:

(1) $R_2^a$ is n-butyl, and $R_2^b$, $R_2^c$, $R_1^c$, $R_2^e$ and $R_3$ are H;

(2) $R_2^a$ is methyl and $R_2^b$, $R_2^c$, $R_1^c$, $R_2^e$ and $R_3$ are H, and (3) $R_2^a$ is H, $R_2^b$ is methyl and $R_2^c$, $R_1^c$, $R_2^e$ and $R_3$ are H.

32. A compound of the formula

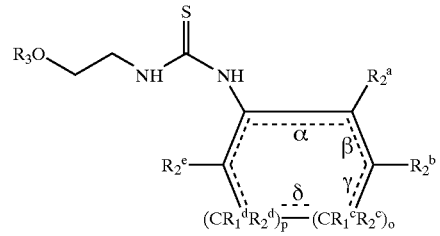

wherein each dotted line represents a bond, or the absence of a bond, with the proviso that only one dotted line represents a bond;

$R_1^c$ is H or does not exist when the adjacent carbon is double bonded;

$R_1^d$ is H or does not exist when the adjacent carbon is double bonded or when p is 0;

$R_2^a$ is H, alkyl of 1 to 4 carbons, F, Cl, Br or l;

$R_2^b$ is H or alkyl of 1 to 4 carbons;

$R_2^c$ is H or alkyl of 1 to 4 carbons;

$R_2^d$ is H or does not exist when p is 0;

$R_2^e$ is H or alkyl of 1 to 4 carbons;

$R_3$ is H or $COCH_3$; o is an integer having the values 1 or 2, and p is an integer having the values 0 or 1.

33. A compound in accordance with claim 32 where o is 1 and p is 1.

34. A compound in accordance with claim 33 where no dotted line represents a bond.

35. A compound in accordance with claim 34 selected from the groups consisting of compounds where:

(1) $R_2^a$ and $R_2^b$ are H, $R_2^c$ is methyl and $R_1^c$, $R_2^d$, $R_1^d$, $R_2^e$ and $R_3$ are H;

(2) $R_2^a$ is n-propyl and $R_2^b$, $R_2^c$, $R_1^c$, $R_2^d$, $R_1^d$, $R_2^e$ and $R_3$ are H;

(3) $R_2^a$ is H, $R_2^b$ is methyl, and $R_2^c$, $R_1^c$, $R_2^d$, $R_1^d$, $R_2^e$ and $R_3$ are H, said compound being an E (trans) isomer;

(4) $R_2^a$ is H, $R_2^b$ is methyl, and $R_2^c$, $R_1^c$, $R_2^d$, $R_1^d$, $R_2^e$ and $R_3$ are H, said compound being a Z (cis) isomer;

(5) $R_2^a$ is methyl, and $R_2^b$, $R_2^c$, $R_1^c$, $R_2^d$, $R_1^d$, $R_2^e$ and $R_3$ are H, said compound being a Z (cis) isomer;

(6) $R_2^a$ and $R_2^b$ are H, $R_2^c$ is ethyl and $R_1^c$, $R_2^d$, $R_1^d$, $R_2^e$ and $R_3$ are H, said compound being an E (trans) isomer;

(7) $R_2^a$ is iso-propyl, $R_2^b$, $R_2^c$, $R_1^c$ are H, $R_2^d$ is methyl and $R_1^d$, $R_2^e$ and $R_3$ are H;

(8) $R_2^a$, $R_2^b$, $R_2^c$, $R_1^c$, $R_2^d$, $R_1^d$, $R_2^D$ and $R_3$ are H;

(9) $R_2^a$ and $R_2^b$ are H, $R_2^c$ is OH, and $R_1^c$, $R_2^d$, $R_1^d$, $R_2^e$ and $R_3$ are H, and

(10) $R_2^a$ is ethyl and $R_2^b$, $R_2^c$, $R_1^c$, $R_2^d$, $R_1^d$, $R_2^e$ and $R_3$ are H, said compound being an E (trans) isomer.

36. A compound in accordance with claim 33 where the dotted line β represents a bond.

37. A compound in accordance with claim 36 selected from the groups consisting of compounds where:

(1) $R_2^a$ is H, $R_2^b$ is methyl and $R_2^c$, $R_1^c$, $R_2^d$, $R_1^d$, $R_2^e$ and $R_3$ are H;

(2) $R_2^a$ is methyl and $R_2^b$, $R_2^c$, $R_1^c$, $R_2^d$, $R_1^d$, $R_2^e$ and $R_3$ are H;

(3) $R_2^a$ is ethyl and $R_2^b$, $R_2^c$, $R_1^c$, $R_2^d$, $R_1^d$, $R_2^e$ and $R_3$ are H;

(4) $R_2^a$, $R_2^b$, $R_2^c$, $R_1^c$, $R_2^d$, $R_1^d$, $R_2^e$ and $R_3$ are H;

(5) $R_2^a$ and $R_2^b$ are methyl and $R_2^c$, $R_1^c$, $R_2^d$, $R_1^d$, $R_2^e$ and $R_3$ are H;

(6) $R_2^a$ is n-propyl and $R_2^b$, $R_2^c$, $R_1^c$, $R_2^d$, $R_1^d$, $R_2^e$ and $R_3$ are H;

(7) $R_2^a$ is Br, and $R_2^b$, $R_2^c$, $R_1^c$, $R_2^d$, $R_1^d$, $R_2^e$ and $R_3$ are H, and (8) $R_2^a$ is H, $R_2^b$ is ethyl and $R_2^c$, $R_1^c$, $R_2^d$, $R_1^d$, $R_2^e$ and $R_3$ are H.

38. A compound in accordance with claim 32 where o is 1 and p is 0.

39. A compound in accordance with claim 38 where no dotted line represents a bond.

40. A compound in accordance with claim 39 where $R_2^a$ is methyl and $R_2^b$, $R_2^c$, $R_1^c$, $R_2^e$ and $R_3$ are H.

41. A compound in accordance with claim 38 where the dotted line β represents a bond.

42. A compound in accordance with claim 41 selected from the groups consisting of compounds where:

(1) $R_2^a$ is H, $R_2^b$ is methyl, $R_2^c$, $R_1^c$, $R_2^e$ and $R_3$ are H;

(2) $R_2^a$ is methyl and $R_2^b$, $R_2^c$, $R_1^c$, $R_2^e$ and $R_3$ are H, and (3) $R_2^a$ and $R_2^b$ are methyl and $R_2^c$, $R_1^c$, $R_2^e$ and $R_3$ are H.

43. A method of activating $\alpha_{2B}$ or $\alpha_{2C}$ adrenergic receptors in a mammal in need of such activation by administering to the mammal a pharmaceutical composition containing a therapeutically effective dose of a compound that has $\alpha_{2B}$ or $\alpha_{2C}$ adrenergic receptor agonist activity and has no significant $\alpha_{2A}$ agonist activity.

44. A method in accordance with claim 43 where the pharmaceutical composition is administered to the mammal to alleviate pain.

45. A method in accordance with claim 43 where the pharmaceutical composition is administered to the mammal to alleviate chronic pain.

46. A method in accordance with claim 43 where the pharmaceutical composition is administered to the mammal to alleviate allodynia.

47. A method in accordance with claim 43 where the pharmaceutical composition is administered orally.

48. A method in accordance with claim 43 where the pharmaceutical composition is administered intraperitonially.

49. A method in accordance with claim 43 where the compound has the formula defined in claim 1.

50. A method in accordance with claim 49 where the pharmaceutical composition is administered to the mammal to alleviate pain.

51. A method in accordance with claim 49 where the pharmaceutical composition is administered to the mammal to alleviate chronic pain.

52. A method in accordance with claim 49 where the pharmaceutical composition is administered to the mammal to alleviate allodynia.

53. A method in accordance with claim 49 where the pharmaceutical composition is administered orally.

54. A method in accordance with claim 49 where the pharmaceutical composition is administered intraperitonially.

* * * * *

UNITED STATES PATENT AND TRADEMARK OFFICE
CERTIFICATE OF CORRECTION

PATENT NO. : 6,534,542 B2
DATED : March 18, 2003
INVENTOR(S) : Chow et al.

It is certified that error appears in the above-identified patent and that said Letters Patent is hereby corrected as shown below:

Title page,
Item [73], Assignee, "Allergen Sales, Inc." should be -- Allergan Sales, Inc. --

Column 2,
Line 34, "Feb. 1, 1978" should be -- February 1, 1978 --

Column 4,
Lines 30-35,   "

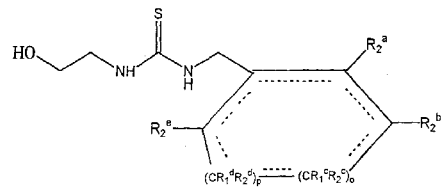

Formula 1 should be   --

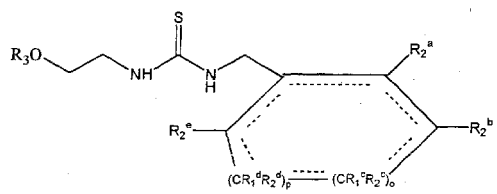

Formula 1

--

Column 5,
Lines 5-10,   "

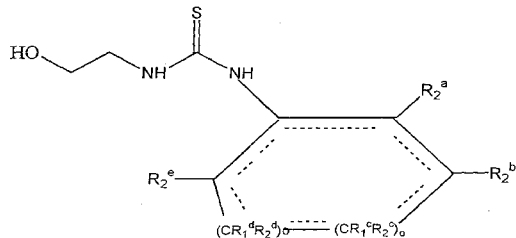

Formula 2

UNITED STATES PATENT AND TRADEMARK OFFICE
CERTIFICATE OF CORRECTION

PATENT NO. : 6,534,542 B2
DATED : March 18, 2003
INVENTOR(S) : Chow et al.

It is certified that error appears in the above-identified patent and that said Letters Patent is hereby corrected as shown below:

Column 5 (cont'd),
should read --

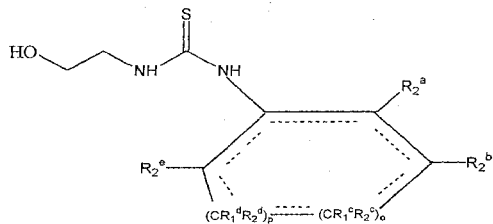

Formula 2

Lines 13-17, within Table 2 "dotted line that represents a double bond" should be
-- dotted line that represents a bond --

Column 8,
Line 64, "UK514304" should be -- UK14304 --

Column 11,
Line 29, "armaceutically" should be -- pharmaceutically --

Column 14,
Line 27, "transyerse" should be -- transverse --

Column 23,
Line 11, "(50% EtOAcihexanes to 10% MeOH/EtOAc)" should be
-- (50% EtOAc/hexanes to 10% MeOH/EtOAc) --

Column 26,
Lines 45-50, "

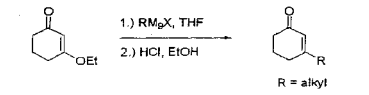

should be --

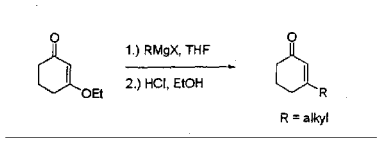

--

UNITED STATES PATENT AND TRADEMARK OFFICE
CERTIFICATE OF CORRECTION

PATENT NO. : 6,534,542 B2
DATED : March 18, 2003
INVENTOR(S) : Chow et al.

It is certified that error appears in the above-identified patent and that said Letters Patent is hereby corrected as shown below:

Column 28,
Line 1, "Synthesis of 2,3-Dimethyl-cyclohex-2-enone" should be -- Synthesis of 2,3-dimethyl-cyclohex-2-enone --

Lines 10-15, "

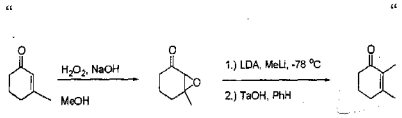

should be --

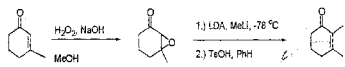

Column 29,
Line 45, "Synthesis of 2-Bromocyclohex-2-enone" should be -- Synthesis of 2-bromocyclohex-2-enone --

Column 31,
Line 46, "3.64-3.73 (in, 2H)" should be -- 3.64-3.73 (m, 2H) --

Column 43,
Line 35, "Acetic Acid 2-(3-Cyclohexymethyl-thioureido)-ethyl Ester" should be
-- Acetic Acid 2-(3-Cyclohexylmethyl-thioureido)-ethyl ester --

Column 45,
Lines 37-38, "(2) $R_2^a$ is H, $R_2^b$ is methyl and $R_2^c$, $R_1C$, $R_2^d$, $R_1^d$, $R_2^e$ and $R_3$ are H;" should be -- (2) $R_2^a$ is H, $R_2^b$ is methyl and $R_2^c$, $R_1^c$, $R_2^d$, $R_1^d$, $R_2^e$ and $R_3$ are H; --
Line 43, "(4) $R_2^a$ is ethyl and $R_2^b$, $R_2^c$, $R_1C$, $R_2^d$, $R_1^d$, $R_2^e$ and $R_3$ are H." should be
-- (4) $R_2^a$ is ethyl and $R_2^b$, $R_2^c$, $R_1^C$, $R_2^d$, $R_1^d$, $R_2^e$ and $R_3$ are H. --

UNITED STATES PATENT AND TRADEMARK OFFICE
CERTIFICATE OF CORRECTION

PATENT NO.  : 6,534,542 B2
DATED       : March 18, 2003
INVENTOR(S) : Chow et al.

It is certified that error appears in the above-identified patent and that said Letters Patent is hereby corrected as shown below:

Column 47,
Line 14, "(8) $R_2^a$, $R_2^b$, $R_2^c$, $R_1^c$, $R_2^d$, $R_1^d$, $R_2^D$ and $R_3$ are H;" should be
-- (8) $R_2^a$, $R_2^b$, $R_2^c$, $R_1^c$, $R_2^d$, $R_1^d$, $R_2^e$ and $R_3$ are H; --

Signed and Sealed this

Seventeenth Day of August, 2004

JON W. DUDAS
*Acting Director of the United States Patent and Trademark Office*